Figure 1A:

United States Patent [19]

Silver et al.

[11] Patent Number: 5,202,120

[45] Date of Patent: * Apr. 13, 1993

[54] METHODS OF REDUCING GLIAL SCAR FORMATION AND PROMOTING AXON AND BLOOD VESSEL GROWTH AND/OR REGENERATION THROUGH THE USE OF ACTIVATED IMMATURE ASTROCYTES

[75] Inventors: Jerry Silver, Lyndhurst; George M. Smith, Cleveland; James W. Jacobberger, Chesterland, all of Ohio

[73] Assignee: Case Western Reserve University, Cleveland, Ohio

[*] Notice: The portion of the term of this patent subsequent to Feb. 13, 2007 has been disclaimed.

[21] Appl. No.: 428,147

[22] Filed: Oct. 27, 1989

Related U.S. Application Data

[63] Continuation-in-part of Ser. No. 96,373, Sep. 11, 1987, Pat. No. 4,900,553.

[51] Int. Cl.$^5$ .................. A61K 35/12; C12N 5/06
[52] U.S. Cl. .................. 424/93 U; 424/425; 424/570; 435/240.2; 435/240.26
[58] Field of Search .................. 424/93, 570, 425; 435/240.2, 240.26; 530/354; 514/801

[56] References Cited

U.S. PATENT DOCUMENTS

| | | |
|---|---|---|
| 4,574,116 | 3/1986 | Kaplan et al. |
| 4,642,291 | 2/1987 | Cairncross et al. |
| 4,662,884 | 5/1987 | Stensaas et al. |
| 4,707,448 | 11/1987 | Major .................. 435/240.25 |

OTHER PUBLICATIONS

Silver, Clin. Res. vol. 36, No. 3, pp. 196–199, 1988.
Janzer et al. Nature, vol. 325, Jan. 15, 1987, pp. 253–257.
Smith et al, J. Comp. Neurol. 251:23–43 (1986).
Wendt, Biol. Abstracts, vol. 80, No. 106569, 1985.
Campbell and Bassett, 1956, Surgical Forum 7:570–574.
Campbell et al., 1957, Science 126:929.
Bassett et al., 1959, Experimental Neurology 1:386–406.
Kalil and Reh, 1979, Science 205:1158–1161.
Silver and Robb, 1979, Dev. Biol. 68:175–190.
Kromer et al., 1980, Brain Res. 210:153–171.
David and Aguayo, 1981, Science 214:931–933.
Kromer et al., 1981, Brain Res., 210:173–200.
Lindsay et al., 1982, Brain Res. 243:329–343.
Silver et al., 1982, J. Comp. Neurol. 210:10–29.
Bottenstein and Sato, Proc. Natl. Acad. Sci. U.S.A. 79:514–517 (1983).
Labbe et al., 1983, Science 221:470–472.
Reier et al., 1983, in "Spinal Cord Reconstruction,", Kao, Bunge, and Reier, eds., Raven Press, New York, pp. 163–195.
Silver and Ogawa, 1983, Science, 220:1067–1069.
Barrett et al., 1984, Exp. Neurol. 84:374–385.
Noble et al., 1984, J. Neurosci 4:1892–1903.
Bernstein et al., 1985, Brain Res. 327:135–141.
Carlstedt, 1985, Brain Res. 347:188–191.
Fallon, 1985, J. Cell Biol. 100:198–207.
Freed et al., 1985, Science 227:1544–1552.
Friedman et al., 1985, J. Neurosci. 5:1616–1625.
Kromer and Cornbrooks, 1985, Proc. Natl. Acad. Sci. U.S.A. 82:6330–6334.
Mathewson et al. 1985, Brain Res. 327:61–69.
Kesslak et al., 1986, Exp. Neurology 92:377–390.

(List continued on next page.)

Primary Examiner—Jacqueline Stone
Attorney, Agent, or Firm—Pennie & Edmonds

[57] ABSTRACT

The present invention relates to "activated" immature astrocytes and the methods of utilizing the activated immature astrocytes as a means for promoting central nervous system nerve growth and regeneration, blood vessel growth and regeneration, and/or reducing secondary necrosis and glial scar formation. The activated immature astrocytes and pharmaceutical compositions comprising same, may be used to treat disorders of the nervous system resulting from trauma or diseases which have in some way damaged the nerve tissue.

57 Claims, 25 Drawing Sheets

OTHER PUBLICATIONS

Manthorpe et al., 1986, in "Astrocytes" vol. 2, Federoff and Vernadakis, eds, Academic Press, New York pp. 315–376.
Schelper et al., 1986, J. Neuropath, and Emper. Neurol. 45:1–19.
Azimitia and Bjorklund, 1987, Annals of the New York Academy of Sciences 495:722–725.
Bunge, 1987, J. Exp. Biol. 132:21–34.
Liuzzi and Lasek, 1987, Science 237:642–645.
Yannas et al., 1987, in "Advances in Biomedical Polymers" Gebelein, ed., Plenum Publishing Corp., pp. 1–9.
Doucette 1984, Anat. Rec. 210–391.
Smith et al., 1987, Ann. N.Y. Acad. Sci. 495:185–206.
Snow et al., 1987, Soc. Neurosci. Abstr. 13:7.
Rudge et al., 1987, Soc. Neurosci. Abstr. 13:290.
Giftochristos and David, 1987 Soc. Neurosci. Abstr. 13:290.
Hoovler et al., 1988, Soc. Neurosci. Abstr. 14:429.
Smith et al., 1988, Soc. Neurosci Abstr. 14:867.
Kliot et al., 1988, Neurol. and Neurobiol. 48:311–328.
Liesi and Silver, 1988, Develop. Biol. 130:774–785.
Smith and Silver, 1988, Prog. Brain Res. 78:353–361.
Rudge et al., 1989, Exp. Biol. 103:1–16.
Goodman et al., 1989, Soc. Neurosci. Abstr. 15:976.
Yong et al., 1988, Growth factors for fetal and adult human astrocytes in culture, Brain Res. 444:59–66.
Frohman et al., The induction of intercellular adhesion molecule 1 (ICAM-1) expression on human fetal astrocytes by interferon-$\gamma$, tumor necrosis factor $\alpha$, lymphotoxin, and interleukin-1: relevance to intracerebral antigen presentation, 1989, J. Neuroimmunol. 23:117–124.

FIG.3a
FIG.3b
FIG.3c
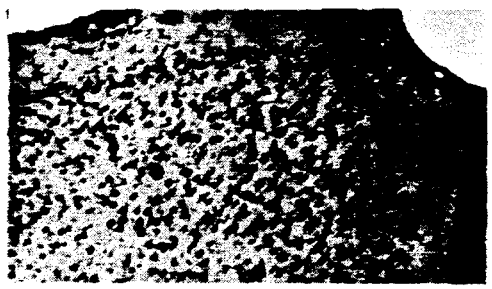
FIG.3d FIG.3e

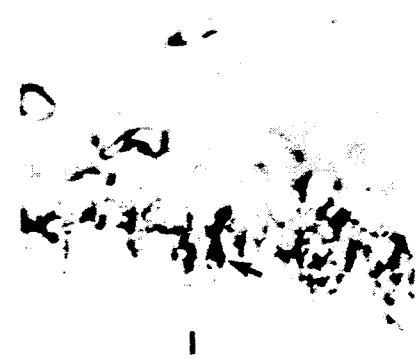
FIG.6a    FIG.6b
FIG.6c    FIG.6d
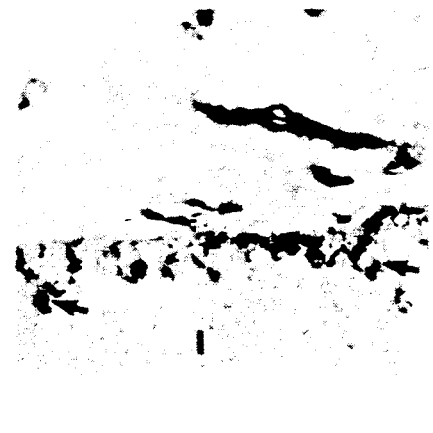
FIG.6e    FIG.6f

FIG.10a  FIG.10b
FIG.10c  FIG.10d

METHODS OF REDUCING GLIAL SCAR FORMATION AND PROMOTING AXON AND BLOOD VESSEL GROWTH AND/OR REGENERATION THROUGH THE USE OF ACTIVATED IMMATURE ASTROCYTES

Pursuant to the provisions of 35 U.S.C. §202(c), it is hereby acknowledged that the Government has certain rights in this invention, which was made in part with funds from the National Eye Institute of the National Institutes of Health.

This application is a continuation-in-part of copending application Ser. No. 096,373 filed Sep. 11, 1987, which is incorporated by reference herein in its entirety, now U.S. Pat. No. 4,900,553.

TABLE OF CONTENTS

1. Introduction
2. Background of the Invention
3. Summary of the Invention
   3.1. Definitions
4. Description of the Drawings
5. Detailed Description of the Invention
   5.1. Activated Immature Astrocytes
   5.2. Methods of Using Activated Immature Astrocytes in the Promotion of Nerve or Blood Vessel Regeneration and/or Scar Reduction
      5.2.1. Treatment of Nerve Injury and Disorders
      5.2.2. Pharmaceutical Compositions
      5.2.3. Modes of Delivery
         5.2.3.1. The Use of Polymer Implants
         5.2.3.2. The Use of Activated Immature Astrocytes in Conjunction with Surgical Bypass Techniques
6. Example: Activated Immature Astrocytes Promote Neural and Blood Vessel Regeneration and Reduce Scar Formation in the Forebrain
   6.1. Materials and Methods
      6.1.1. Transportation of Implants and Cellular Coatings
         6.1.1.1. Insertion of the Implants
         6.1.1.2. Removal of the Implants Plus Their Cellular Coatings
         6.1.1.3. Transplantation of the Implants and Their Cellular Coatings To Older Postcritical Period Hosts
      6.1.2. Immunohistochemistry
      6.1.3. Horseradish Peroxidase Injections
      6.1.4. $^3$H-thymidine Autoradiography of Transplants
   6.2. Results
      6.2.1. Determination of the "Critical Period" in Astrocytes for Axon Elongation
      6.2.2. Determination of the Location of the Cell Bodies that Contributed Axons to the Implant Surface
      6.2.3. Host Glial Response to Nitrocellulose Bridges Implanted at Various Postnatal Ages
      6.2.4. Extracellular Matrices Associated With Gliotic Response at Different Ages
      6.2.5. Axon Reaction to Flattened Astrocytes in Postnatal Day 2 Neonates Induced by Compressing the Pores of the Implant
      6.2.6. Transplantation of Glial-Coated Implants From Neonatal to Post-critical Period Animals
      6.2.7. Induced Axon Growth Over Glial Transplants
   6.3. Discussion
7. Example: Transplantation of Purified Activated Immature Astrocytes into Postcritical Period Animals
   7.1. Materials and Methods
      7.1.1. Preparation of Purified Activated Immature Astrocytes
      7.1.2. Preparation of Mature (P14or Older) Astrocytes
      7.1.3. Seeding of the Nitrocellulose Implants
      7.1.4. Implantation of the Glial-Coated Filters
         7.1.4.1. In the Forebrain of the Postnatal Day 60 Acallosal Mice
         7.1.4.2. In the Dorsal Root Entry Zone of the Spinal Cord of the Postnatal Day 180 or Older Rats
      7.1.5. Immunohistochemistry and $^3$-Thymidine Autoradiography of the Transplants
   7.2. Results
      7.2.1. Transplantation of Purified Astrocytes into the Forebrain
      7.2.2. Transplantation of Purified Activated Immature Astrocytes into the Dorsal Root of the Spinal Cord
8. Example: Immortalization of the Activated Immature Astrocytes
9. Example: Astrocyte Maturation Reduces Neurite Outgrowth and Neuronal Adhesion in Vitro
   9.1. Materials and Methods
      9.1.1. Preparation of Purified Astrocytes
      9.1.2. Preparation of Cortical Neurons
      9.1.3. Quantitation of Neurite Outgrowth
      9.1.4. Short Term Neuronal Adhesion Assay
      9.1.5. Electron Microscopy
   9.2. Results
      9.2.1. Neuronal Morphology on Immature and Mature Astrocytes
      9.2.2. Differences in Neurite Outgrowth Over Immature and Mature Astrocytes
      9.2.3. Neurite Outgrowth in the Presence of Conditioned Medium From Immature and Mature Astrocytes
      9.2.4. Neuron Adhesion to Immature and Mature Astrocytes
      9.2.5. Ultrastructural Characteristics of Immature and Mature Astrocytes
   9.3. Discussion
10. In Vitro Analyses of Astrocytes Cell Interactions of Different Ages
11. Induced Regeneration of Cut Dorsal Root Fibers into Adult Rat Spinal Cord
12. Analysis of Neonatal and Adult Rat Olfactory Bulb Glial Cell Lines
13. Deposit of Microorganism

1. INTRODUCTION

The present invention relates to "activated" immature astrocytes and the methods of utilizing the activated immature astrocytes as a means for reducing secondary necrosis and glial scar formation, as well as promoting blood vessel and central nervous system axon growth and/or regeneration. The activated immature astrocytes and pharmaceutical compositions comprising same, may be used to treat disorders of the nervous system resulting from trauma or diseases which have in some way damaged the nerve tissue.

2. BACKGROUND OF THE INVENTION

In the central nervous system, the chief non-neural cells are the glial cell types. These vary in numbers and type from one part of the nervous system to another, but the two basic classes can be distinguished by their size and embryonic origin, namely the macroglia, which are relatively large cells derived from the neural plate, and the smaller microglia which stem from the mesodermal tissues surrounding the nervous system.

The macroglia comprise two cell types, the astrocytes (astroglial cells) and the oligodendrocytes (oligodendroglial cells).

Astrocytes possess small cell bodies (the nucleus is about 8 microns in diameter in man) with ramifying dendrite-like extensions. The cytoplasmic processes of astrocytes carry fine, foliate extensions which partly engulf and separate neurons and their neurites, and often end in plate-like expansions on blood vessels, ependyma and on the pial surface of the central nervous system.

The functions of astrocytes are numerous. They act mechanically as a supporting component of the nervous system. Their microfilaments, microtubules, and surface contact zones fit them for this task. They also act defensively by phagocytosing foreign material or cell debris. They can function as antigen presenting cells to macrophages and can provide a means of limited repair by forming glial scar tissue or filling the gaps left by degenerated neurons. In addition, they have essential metabolic functions in regulating the biochemical environment of neurons, providing nutrients, and regulating acid-base levels, etc.

Moreover, the astrocytes, which are able to divide in immature and mature animals, pass after mitosis through a series of structural transformations depending on their state of maturity. In areas of brain injury in young or old animals they proliferate (gliosis) to produce neural support. In a penetrating injury to the central nervous system (CNS) of adult mammals, severe tissues damage and secondary necrosis occurs in the region surrounding the wound. The degenerating effects caused by the injury are believed to generate a response in the surviving glial cells adjacent to the site of the injury (Reier et al., 1983, The Astrocytic Scar As an Impediment to Regeneration in the Central Nervous System, Spinal Cord Reconstruction, Raven Press, N.Y., pp. 163-195). The astrocyte response consists of a slight mitotic increase, an increase in size (hypertrophy), and a concomitant increase in quantity of intermediate filaments (Mathewson, et al., 1985, Brain Res. 327:61-69). Together with invading monocytes, the astrocytes act as phagocytes to clear debris within the wound cavity (Schelper, et al., 1986, J. Neuropath. and Exper. Neurol. 45:1-19). When the injury disrupts the plial lining of the brain, fibroblasts migrate into the wound cavity and multiple layers of basal lamina form over the astrocyte surface (Bernstein, et al., 1985, Brain Res. 327:135-141). The fibroblasts also produce collagen, which forms dense bundles within the surrounding extracellular spaces several weeks after injury. Thus, in adults the astrocytes, together with other cellular elements, form dense interwoven scars which fill the space vacated by the dead or dying cells in the injury area. Although the scar may help save the organism it also blocks axonal regeneration and the individual is left with an irreversible functional deficit or epileptic focus depending on the site of the lesion.

Previous studies by the inventors and others indicated that penetrating lesions in the central nervous system (CNS) of neonatal mammals rarely resulted in the formation of glial scars similar to those observed in adults and that the production of typical adult glial scars after injury increased after the first two postnatal weeks in rodents (Barrett, et al., 1948, Exp. Neurol. 84:374-385; Smith, et al., 1986, J. Comp. Neurol. 251:23-43).

Previous studies on regeneration have demonstrated that CNS axons have the potential to grow long distances through peripheral nerve grafts (Friedman, et al., 1985, J. Neurosci. 5:1616-1625) or Schwann cell bridges (Kromer, et al., 1985, Proc. Natl. Acad. Sci. U.S.A. 82:6330-6334). However, the studies with peripheral nerve elements indicated that regenerating nerve fibers could only extend a short distance upon reentry into the CNS, most likely due to the formation of scars at the ends of the graft. In addition, after repeatedly crushing or cutting the dorsal roots near their entrance point in the spinal cord, the peripheral sensory fibers are regenerated only as far as the dorsal root entry zone (DREZ) of the spinal cord but no further. The problem at the DREZ is analogous to the failure of axon regeneration throughout the remainder of the CNS. Although the distance needed to reconnect the regenerating sensory fibers with their denervated dendrites in the dorsal horn of the spinal cord is relatively short (i.e., only fractions of a millimeter in the adult rat), this scant distance is normally never breached by regenerating sensory fibers in adult animals. Thus, although the injured adult CNS is potentially capable of a considerable amount of regeneration, sprouting is usually abortive and the axons fail to reinnervate their appropriate targets.

In addition, studies by the inventors indicated that developing axons are guided by oriented "highways of astroglial tissues" (Silver, et al., 1979, Dev. Biol. 68:175-190; Silver, et al., 1982, J. Comp. Neurol., 210:10-29).

The inventors have shown that in early postnatal lesion-induced acallosal animals, an untreated, properly shaped nitrocellulose (Millipore) filter, placed adjacent to the neuromas and spanning the lesioned cerebral midline, can support the migration of immature glia (Silver, et al., 1983, Science, 220:1067-1069).

3. SUMMARY OF THE INVENTION

The present invention is directed to "activated" immature astrocytes, pharmaceutical compositions comprising the same, and methods of utilizing the activated immature astrocytes to treat patients with damage to the nervous system. According to the present invention, it has now been determined that contrary to normal adult astrocytes which promote glial scar formation, certain "critical period" activated immature astrocytes reduce glial scar formation, inhibit extensive bleeding and secondary necrosis, and promote central nervous system axonal regeneration. Thus, the activated immature astrocytes can be administered therapeutically, to promote axon regeneration in the central nervous system, to promote blood vessel regeneration, and/or to reduce glial scar formation and necrosis.

One embodiment of the present invention concerns the use of "activated" immature astrocytes in injectable form or on implants to promote directed axon regeneration and reduce glial scar formation in the forebrain, or in damaged spinal axons of the central nervous system.

The invention is illustrated by way of example infra, wherein activated immature astrocytes (murine postnatal day 8 or less) were harvested and transplanted into postcritical period animals (postnatal day 14 or more) in order to determine whether an environment conducive for axon regeneration could be re-established in the postcritical animals. The results (discussed in more detail below) indicate that the immature astrocytes survive implantation and reduce the deleterious sequelae of lesions in the brain. In addition, axonal regeneration and/or blood vessel growth was enhanced. The beneficial effects observed included the reduction of necrosis and glial scar formation at the lesion site, as well as the stimulation and promotion of a substratum for the regeneration of postcritical period callosal axons that were not otherwise observed to regenerate. Although the initial studies were performed with activated immature astrocytes (postnatal day 8 or less) harvested on millipore filters placed in the forebrain of postcritical period mice, further examples, presented herein, indicated that the same beneficial effects are observed when the activated immature astrocytes are implanted on polymers in the spinal cord region of paralyzed animals.

In addition, the activated immature astrocytes have been isolated, harvested, and purified in vitro for use in vivo as well as in vitro. In addition, because normal immature astrocytes mature in culture, purified activated immature astrocytes have been genetically engineered to be immortal and forever immature for in vivo therapeutic use. Similarly, the activated immature astrocytes have been used in vitro to promote axon growth in biological cultures.

3.1. DEFINITIONS

As used herein, the following terms shall have the meanings indicated:
BSA = bovine serum albumin
CMF = calcium-, magnesium-free buffer
CNS = central nervous system
DNase = deoxyribonuclease
DMEM = Dulbecco's modified Eagle's medium
DREZ = dorsal root entry zone
FCS = fetal calf serum
GFAP = glial fibrillary acid protein
HRP = horseradish peroxidase
Ig = immunoglobulin
NGS = normal goat serum

4. DESCRIPTION OF THE FIGURES

Figure 1B:
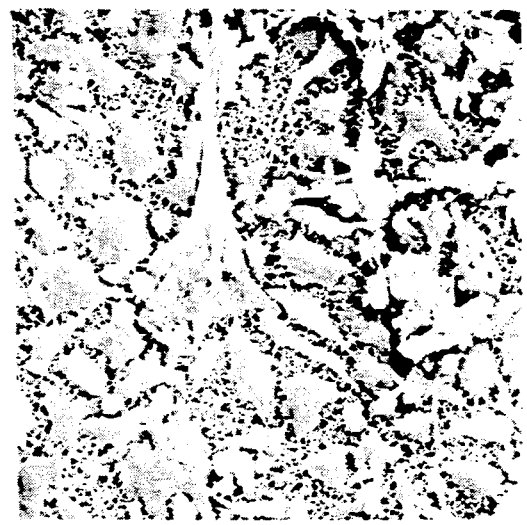
Figure 1C:
Figure 1D:
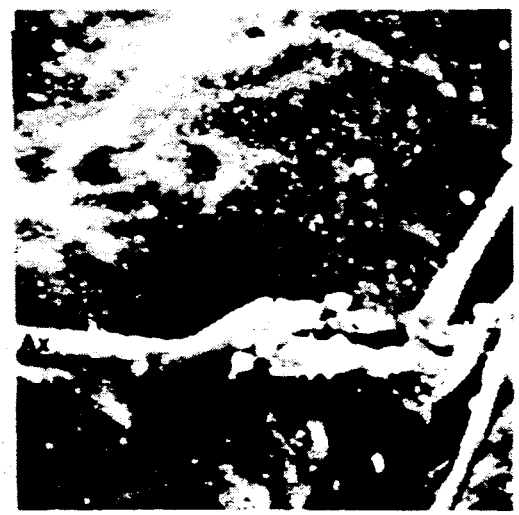

FIGS. 1a, 1b, 1c, and 1d are scanning electron micrographs of acallosal mice implanted on postnatal day 2 and examined 24 hours later. In FIG. 1a, a brain viewed from above shows a filter (I) that was placed horizontally across the midline extending into each cortical hemisphere. Higher magnification of the surface of the filter showing many attached cells is illustrated in FIG. 1b. As shown in FIG. 1c, the first axons (arrowheads) to extend across the filter do so nonfasciculated and along the glia that have attached to the implant. FIG. 1d shows that astrocytes respond to the presence of axons (Ax) by extending small processes (arrow) that encircle the axons. The magnification of the respective FIGURES is as follows: (a) ×20; (b) ×700; (c) ×2,000; (d) ×16,000.

Figure 2A:
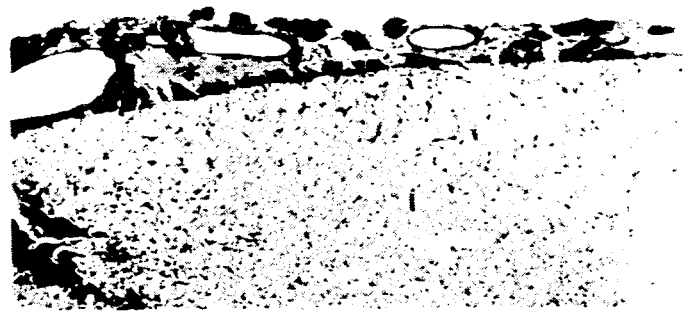
Figure 2B:
Figure 2C:
Figure 2D:
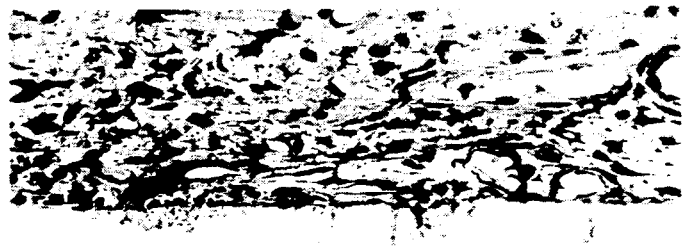
Figure 2E:

FIGS. 2a, 2b, 2c, 2d, and 2e are micrographs of coronal sections through the nitrocellulose bridge (I) and associated tissue of the hemispheric midline of acallosal mice. FIGS. 2a-2c represent animals implanted at "critical" stages; postnatal days 2 (FIG. 2a) and 8 (FIGS. 2b, 2c), both examined 48 hours after implantation. A comparison of FIGS. 2a-2c to animals implanted at "postcritical" stages, 14 (FIG. 2d) and 21 (FIG. 2e) days after birth, both examined 7 days postoperatively, indicate that in FIGS. 2a-2c the glia are more stellate, sending many cytoplasmic processes into the pores of the filter, whereas the cells near the implant in FIG. 2d and FIG. 2e appear flat, lacking extensive infiltration of processes. Directly above the infiltrated stellate glia of "critical" period implants are numerous axons (asterisks; FIGS. 2a-2c), but such axons were not apparent in "postcritical" stage implants (FIGS. 2d-2e). The magnification of the respective FIGURES is as follows: (a) ×400; (b) ×125; (c) ×400; (d) ×400; (e) ×400.

FIGS. 3a, 3b, 3c, 3d, and 3e are micrographs of the corpus callosum of a previously acallosal animal implanted with a Millipore implant on postnatal day 5. When the animal was killed five weeks later, a new callosum (CC) had formed above the implant (FIGS. 3b and 3c). Further rostrally the bridge did not span the midline and was embedded in only one of the neuromas (FIG. 3a). In this region small groups of axons left the neuroma but grew ectopically along the subependymal zone within the dorsal septum (*). Uniquely, the animal had both large longitudinal neuromas (LB) and a well-developed callosum in the same plane of section as well as the ectopic ipsilateral septal projection (FIGS. 3b and 3c). This uniqueness provides a marker that ensures that the animal was acallosal at the time of implantation. Horseradish peroxidase injected into the cortex of one hemisphere in the region of the de-novo-formed callosum (arrow) labels neurons on the opposite side of the brain (bracketed area of FIG. 3c; higher magnification, FIGS. 3d and 3e). The reformed callosum has grown to its appropriate region of synaptic termination (small arrows). The magnification of the respective FIGURES is as follows: (a) ×100; (b) ×100; (c) ×100; (d) ×250; (e) ×400.

Figure 4A:
Figure 4B:
Figure 4C:

FIGS. 4a, 4b, and 4c are micrographs of coronal sections through filters implanted into postnatal day 2 acallosal mice and examined 24 (FIG. 4a), 48 (FIG. 4b), and 72 (FIG. 4c) hours later. In FIG. 4a, twenty-four hours after implantation, numerous glia (arrowheads), some of which are phagocytic (insert), have migrated out of the hemisphere and along the implant. As they attach to the implant (I) they extend cytoplasmic processes into the pores of the filter (small arrows in FIGS. 4b and 4c); note that the leading glial cell (far right) has extended few processes. In FIG. 4b, within 48 hours, glia coat the majority of the filter surface, providing a substrate on which axons (Ax) and blood vessels have extended. As shown in FIG. 4c, in some specimens 72 hours after implantation, the axons fasciculate over the glia above the filter, a configuration similar to that of the normal developing corpus callosum and "sling". Note in FIG. 4c however, the absence of a glial limiting membrane. The magnification of the respective FIGURES is as follows: (a) ×500; (b) ×400; (c) ×500; insert ×4,400.

Figure 5A:
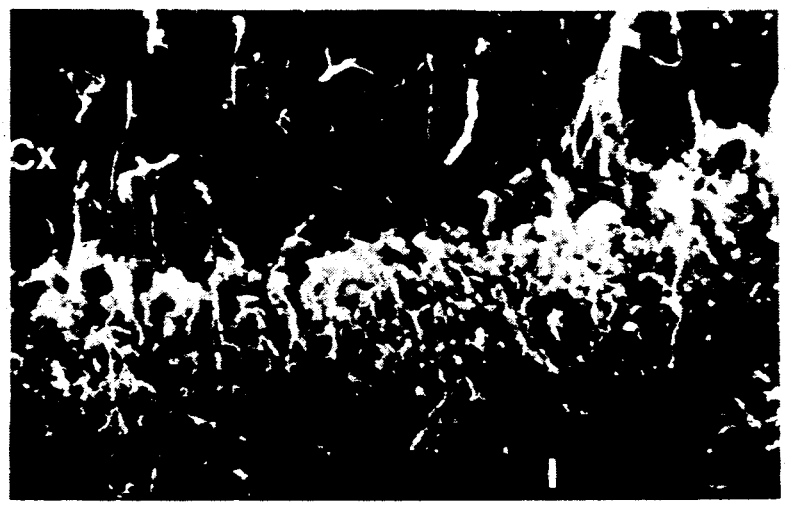
Figure 5B:
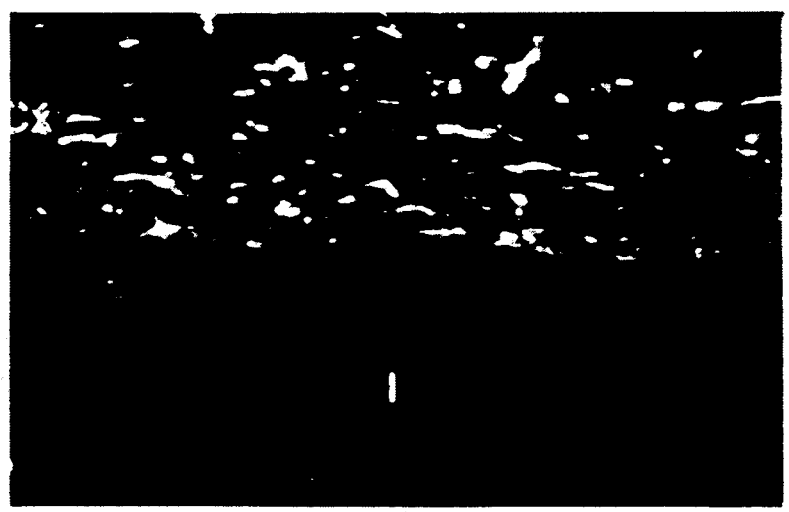

FIGS. 5a and 5b are micrographs of coronal sections illustrating the staining pattern for antibodies against GFAP in animals implanted at critical and postcritical ages. In FIG. 5a, acallosal neonates (P2) implanted with filters and examined after five days show extensive astrocytic processes within the implant (I) and within the cortex (Cx), retaining their stellate morphology. In FIG. 5b, the astrocytes in acallosal animals implanted at postcritical stages (P21) and examined after one week appear flat within the scar above the implant (I). The magnification of the respective FIGURES is as follows: (a) ×300; (b) ×300.

FIGS. 6a, 6b, 6c, 6d, 6e, and 6f are micrographs of coronal sections showing the staining pattern produced by antibodies against laminin protein. As shown in FIG. 6a, in critically implanted before P8 animals laminin not only appears to be confined to the basal lamina of blood vessels and the pia, but it is also along glial processes (arrows) within the filter (FIGS. 6a and 6b). When animals were implanted at postcritical stage (P21) antilaminin stained the basal lamina in the scar that extends around the implant (I) and appears continuous with the longitudinal fissure (LF; FIGS. 6c and 6d). The cells producing the laminin are flat. Post-critical period animals P34 (FIGS. 6e, 6f) implanted with glial-coated filters from P2 neonates show no scar formation and thus, a laminin staining pattern identical to critical period animals given naked implants alone (compare FIGS. 6a and 6b to FIGS. 6e and 6f). The magnification of the respective FIGURES is as follows (a) ×100; (b) ×250; (c) ×100; (d) ×250; (e) ×100; (f) ×250.

Figure 7A:
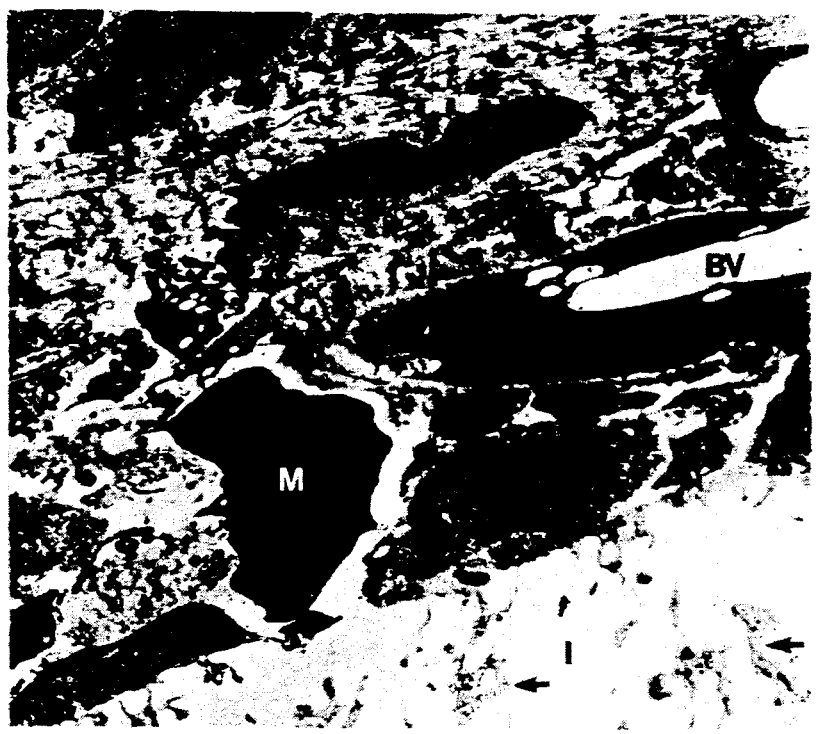
Figure 7C:
Figure 7C:
Figure 7B:
Figure 7D:

FIGS. 7a, 7b, 7c, and 7d are transmission electron micrographs of acallosal mice implanted 8 days after birth and killed 48 hours later. In FIG. 7a, glia attached to the implant have a stellate morphology; microglia (M) are also apparent. Among and above the glia that have sent processes into the filter (arrows) are axons (Ax) and blood vessels (BV). As noted in FIG. 7b, the axons (small arrows) that extend into areas where basal lamina (BL arrowheads) appear are positioned immediately adjacent to the glia but not to the basal lamina. Higher magnification in FIGS. 7c and 7d shows axons associated with astrocyte processes (G) containing intermediate filaments and glycogen granules. The magnification of the respective FIGURES is as follows: (a) ×4,500; (b) ×5,000; (c) ×12,000, and (d) ×12,000.

Figure 8A:
Figure 8B:
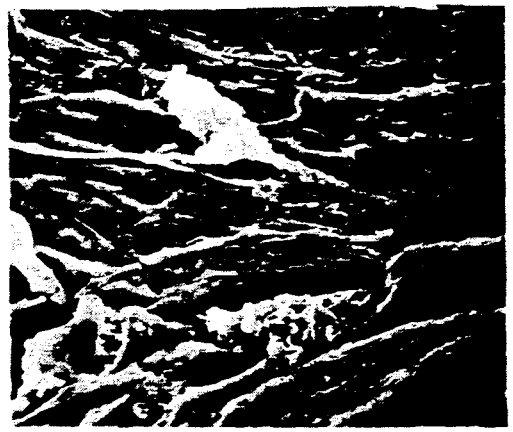
Figure 8C:
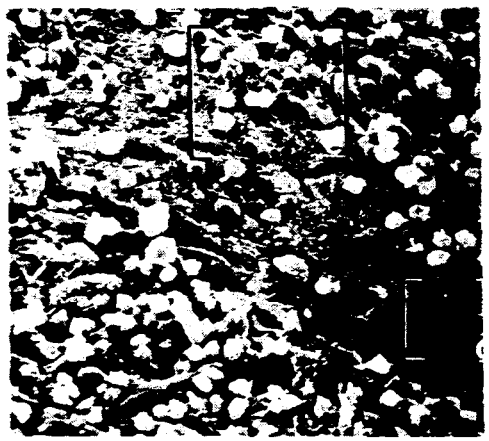
Figure 8D:
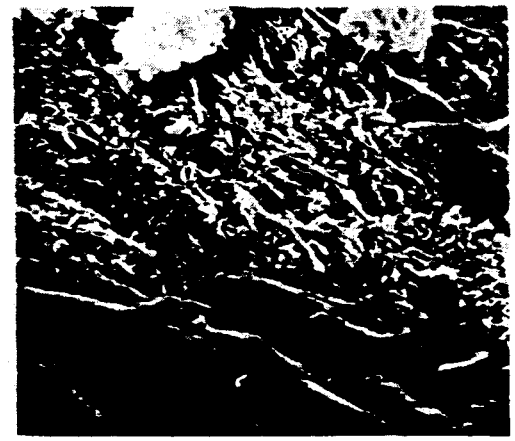
Figure 8E:
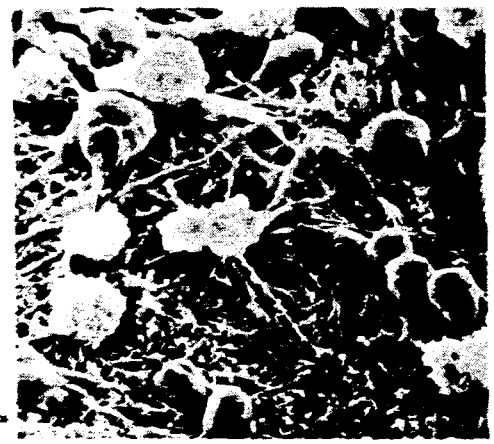
Figure 8F:
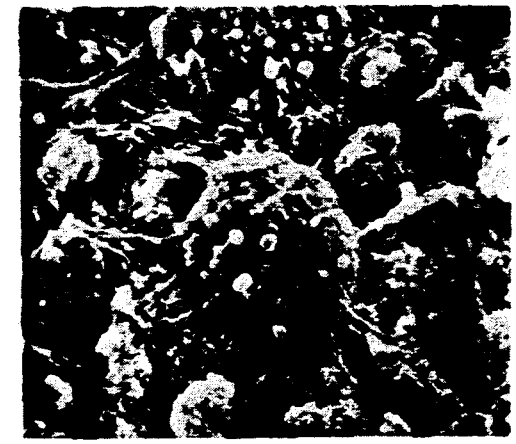

FIGS. 8a, 8b, 8c, 8d, 8e, and 8f are scanning electron micrographs of acallosal mice implanted on postnatal day 2 with partially crushed filters and examined 48 hours later. In FIG. 8a, the glia above the crushed portion of the filter (C) are flat and have a smooth surface (FIGS. 8a and 8b), whereas the glia attached to the noncrushed area (NC) are more stellate in shape (FIGS. 8a, 8b, and 8f). In places, some of the flat glia over the crushed implant, rippled and extended many very short processes (FIG. 8d). In areas where this occurred, other glia moved onto the flattened cells establishing a cellular pile (FIG. 8e). The magnification of the respective FIGURES is as follows: (a) ×200; (b) ×1,800; (c) ×600; (d) ×3,500; (e) ×1900; (f) ×2,100.

Figure 9A:
Figure 9B:

FIGS. 9a and 9b are micrographs of coronal sections of postnatal day 27 (P27) animals that received transplanted filters precoated with glia from neonates that were injected with $^3$H-thymidine. In FIG. 9a, a majority of the glia attached to the filters labeled with silver grains over the nuclei. Cells further removed from the implant surface and along blood vessels are also labeled by $^3$H-thymidine (arrows). Transplanted neonatal glia on Millipore (I) placed into post-critical-period animals (P34) retain their stellate morphology, as shown when stained with antibodies against GFAP (see FIG. 9b). The magnification of the respective FIGURES is as follows: (a) ×450; (b) ×300.

FIGS. 10a, 10b, 10c, and 10d are micrographs of coronal sections of untreated implants placed into postcritical acallosal animals (FIGS. 10a and 10b) and transplanted filters precoated with glia harvested from neonates (FIGS. 10c and 10d). The reacting cells along the untreated filter (FIGS. 10a and 10b), are arranged in sheets and have a flattened morphology, with a few processes extending into the implant. In contrast, the gliotic reaction produced in the postcritical brain by the transplant resembles critical period implanted animals. Numerous inserted processes (arrowheads) from stellate cells and minimal scar formation or necrosis are evident (FIGS. 10c and 10d). The magnification of the respective FIGURES is as follows: (a) ×125; (b) ×400; (c) ×125; (d) ×400.

Figure 11:

FIG. 11 is a transmission electron micrograph of the host/donor interface (far lateral to the midline) from a P17 acallosal animal that was given a precoated glial implant (transplant) and examined after six days. The astrocytes attached to the implant (I) retain their inserted processes which are rich in intermediate filaments (arrow). The cortex above the attached glia shows little tissue degeneration and no scar formation. The magnification in FIG. 11 is ×12,600.

Figure 12A:
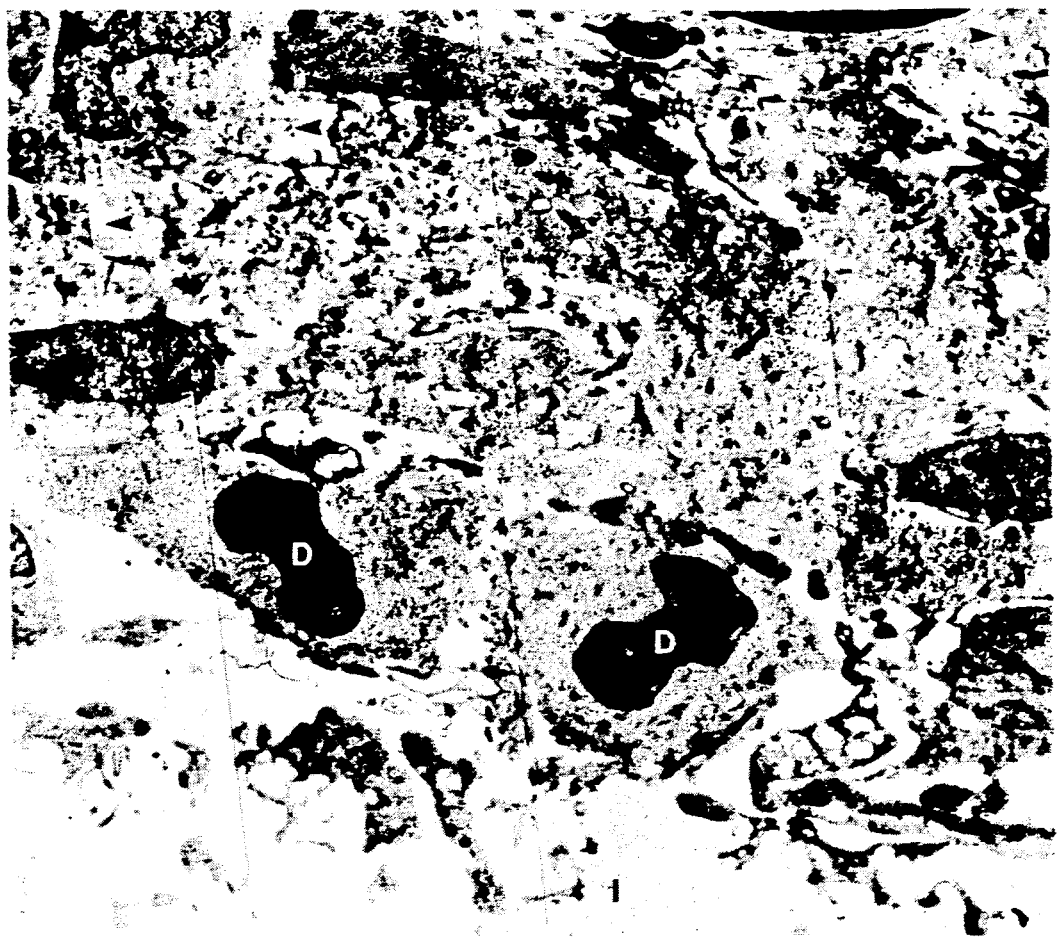
Figure 12B:
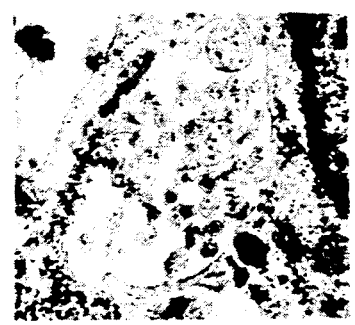
Figure 12D:
Figure 12C:
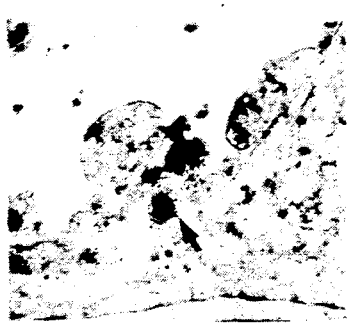

FIGS. 12a, 12b, 12c, and 12d are transmission electron micrographs at the midline of a postnatal day 17 acallosal mouse that received a pre-glial coated implant (I) from a 2-day neonate donor and was then examined six days after it resided in the host. As shown in FIG. 12a, the glia attached to the implant have retained their stellate morphology and infiltrated cytoplasmic processes. Scarring and ectopic basal lamina are absent. Among the glia are many de-novo-formed axon bundles (arrowheads). Higher magnification shows loosely fasciculated unmyelinated axons (FIG. 12b) and others (arrow) adjacent to astrocytic processes. Two daughter cells (D) above the implant share a midbody (open arrow in FIG. 12d). Thus, transplanted cells can divide. The magnification of the respective FIGURES is as follows: (a) ×10,000; (b) ×20,000; (c) ×10,000; (d) ×3,300.

Figure 13A:
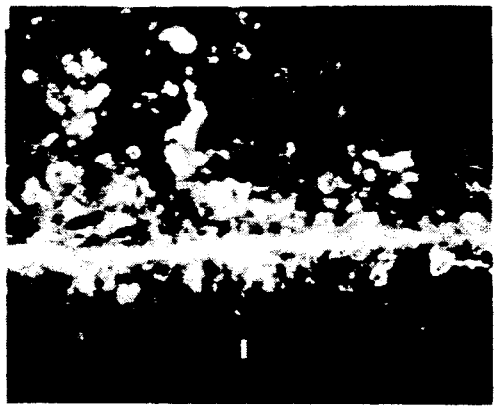
Figure 13B:
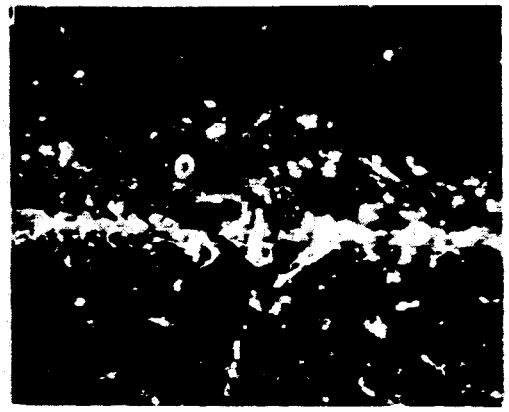
Figure 13C:
Figure 13D:
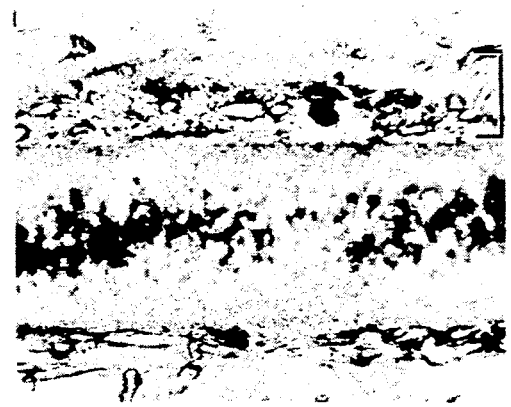
Figure 13E:
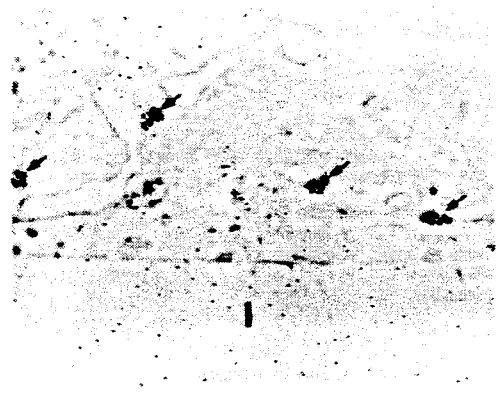
Figure 13F:

FIGS. 13a, 13b, 13c, 13d, 13e, and 13f are micrographs of GFAP immunofluorescence. These micrographs show that both immature (FIG. 13a) and mature (FIG. 13b) astrocyte coated implants (I) have GFAP positive astrocytes attached to their surface. Astrocytes were purified and allowed to age in vitro. Photomicrographs of laminin immunoreactivity in P60 acallosal mice transplanted with either immature (FIG. 13c) or mature (FIG. 13d) astrocyte coated implants. Note the lack of basal lamina staining (i.e. scarring) in the host brain receiving immature astrocytes (bracket in FIG. 13c). However, basal lamina is quite apparent in host brains receiving mature astrocyte coated implants (bracket in FIG. 13d). Basal lamina staining on the bottom of all tansplants is caused by the lack of transplanted astrocytes in that portion since they were seeded on the top of the filters in culture. Autoradiograph of astrocytes transplanted into P60 mice which were labeled with $^3$H-thymidine in culture. Labeled immature astrocytes (arrows) have the ability to migrate away from the surface of the implant (FIG. 13e). Labeled mature astrocytes (arrowheads) did not appear to migrate away from the surface in the implant (FIG. 13f). The magnification of the respective FIGURES is as follows: (a) ×400; (b) ×400; (c) ×300; (d) ×300; (e) ×400; (f) ×400.

Figure 14A:
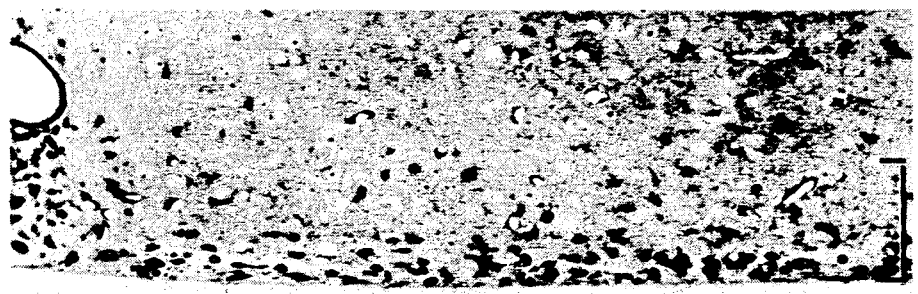
Figure 14B:
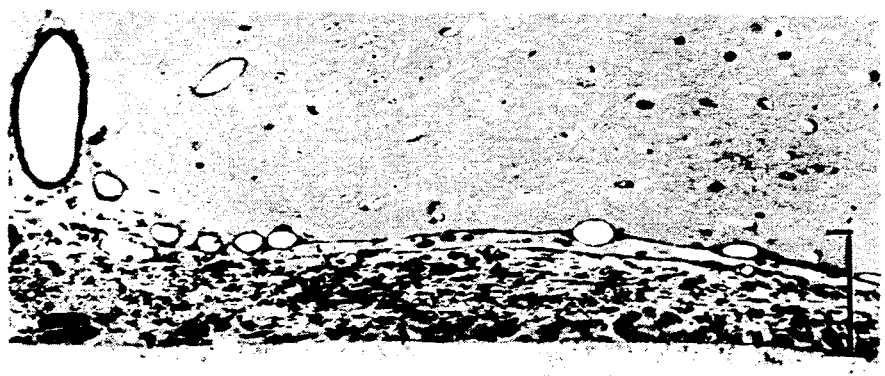

FIGS. 14a and 14b are photomicrographs of immature (FIG. 14a) and mature (FIG. 14b) astrocyte coated filters (I) which were implanted into P60 acallosal mice. Host brains of animals implanted with immature astrocytes (culture 4 days) had minimal scar formation and tissue degeneration (area in bracket in FIG. 14a). In contrast, the site of injury around implants coated with mature astrocytes (28 or more days in culture) developed a glial-mesenchymal scar similar to that observed in adult mice implanted with untreated filters (area in bracket in FIG. 14b). The magnification of the respective FIGURES is as follows: (a) ×400; (b) ×400.

Figure 15A:
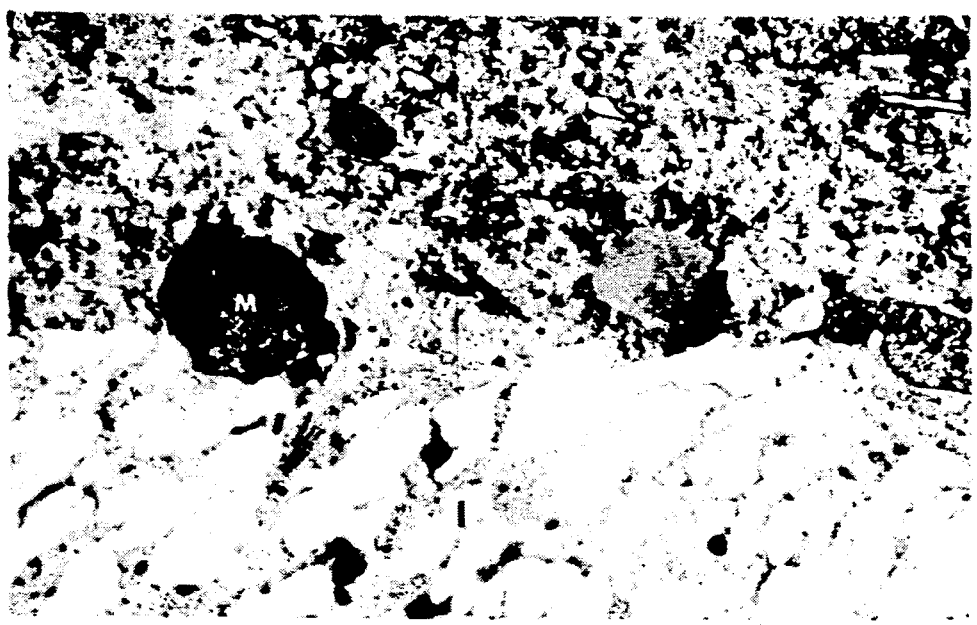
Figure 15B:

FIGS. 15a and 15b are transmission electron micrographs of the surface of an immature astrocyte coated implant (I) which was transplanted into a P60 acallosal mouse. Astrocytes containing intermediate filaments (gf) cover much of the surface of the implant (FIGS. 15a and 15b). However, there still exists a few monocytes (M) and small pockets of basal laminae (arrowheads). In the region of the cortex above the implant are intacted neutrophils containing unmyelinated and myelinated axons (arrows). Transmission electron micrograph of the scar that formed in response to the transplantation of a mature astrocyte coated implant (I) into a P60 acallosal mouse. The glial-mesenchymal scar contains collagen (cf), fibroblasts (large arrowheads) and basal laminae (small arrowheads) and fibroblasts (FIG. 15b). The magnification of the respective FIGURES is as follows: (a) ×4,400; (b) ×4,400.

Figure 16:
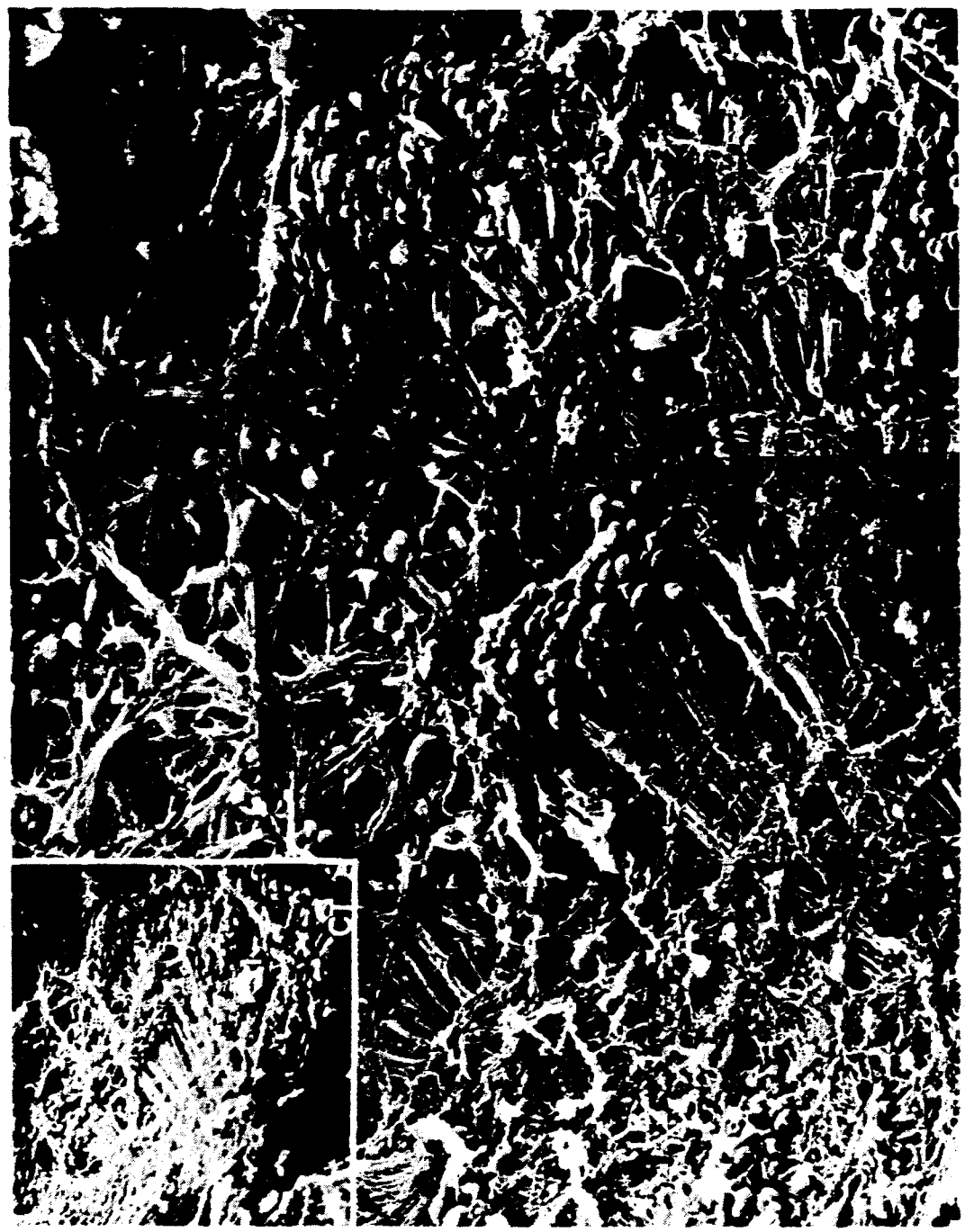

FIGS. 16a and 16b are scanning electron micrographs of axons extending over the glia (asterisk) attached to a filter implanted into an acallosal postnatal (day 2) and examined 48 hours later. The low power insert (FIG. 16a) shows callosal axons extending from only one hemisphere, out of the neuroma (LB) and across the implant (I) The caudal tip (CT) and borders of the filter are apparent. Higher magnification (FIG. 16b) shows large fascicles of axons traversing the implant towards the opposite hemisphere. However, not all axons retain their orientation and some wander in the middle of the filter (arrows). The magnification of the respective FIGURES is as follows: (a) ×80; (b) ×700.

Figure 17A:
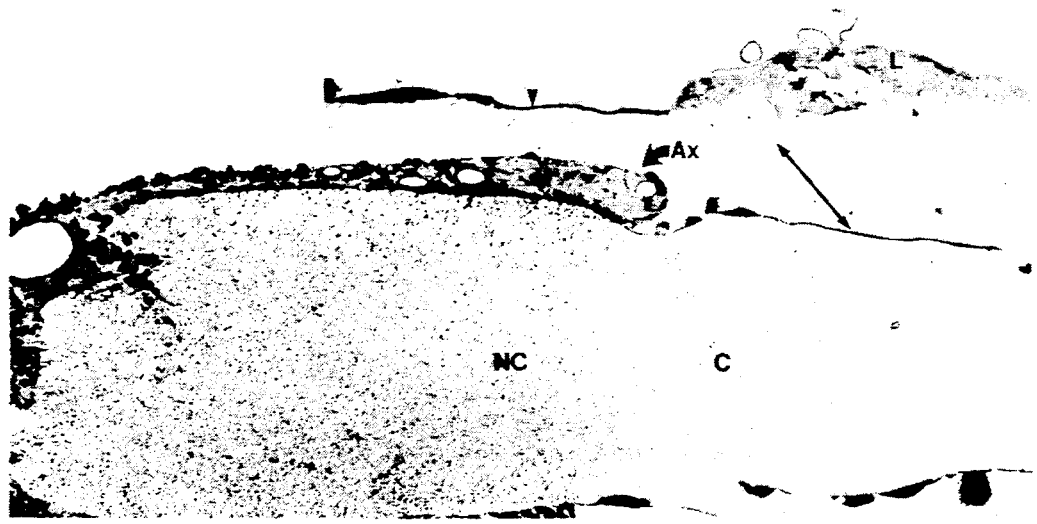
Figure 17B:
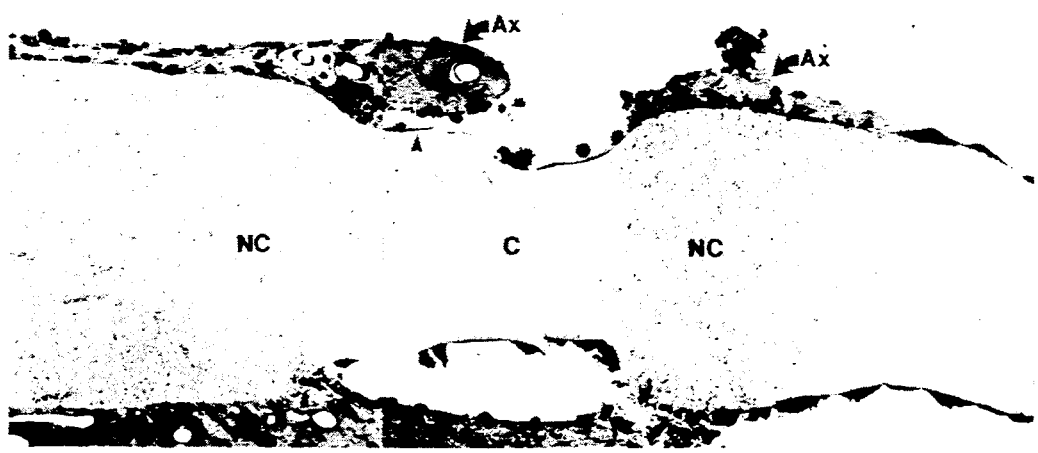
Figure 17C:
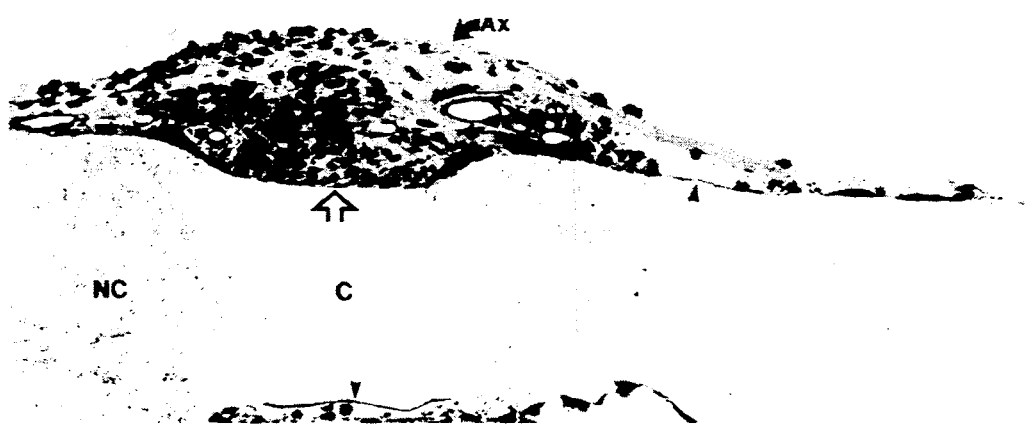

FIGS. 17a, 17b, and 17c are micrographs of coronal sections through a partially crushed filter implanted into a postnatal day 2 acallosal mouse and sacrificed 48 hours later. In FIG. 17a, the axons (Ax) traverse the surface of the implant along the stellate "activated" glia (i.e. inserted) that extend processes into the non-crushed portion of the filter (NC), but they turn abruptly at the crush (C)/non-crush (NC) interface. The astrocytes attached to the surface of the crushed portion were non-activated flattened (arrowheads and upper insert), displayed a mound where the nuclei reside and had lamellipodia (L in second insert) at their periphery. As noted in FIG. 17b, the axon bundle (Ax) turns perpendicularly and travels along the crush/non-crush interface. In FIG. 17c, fibers crossed over the crushed portion of the implant above a mat of glia with a flat-celled bottom layer (open arrow). The fibers then grew rostrally on another inserted group of cells on the other side of the crush (Ax at the right in FIG. 17b). Some axons were also present within the filter on the inserted activated astroglial processes. The magnification of the respective FIGURES is as follows: (a) ×400; (inserts) ×625; (b) ×3,300; (c) ×400.

Figure 18A:
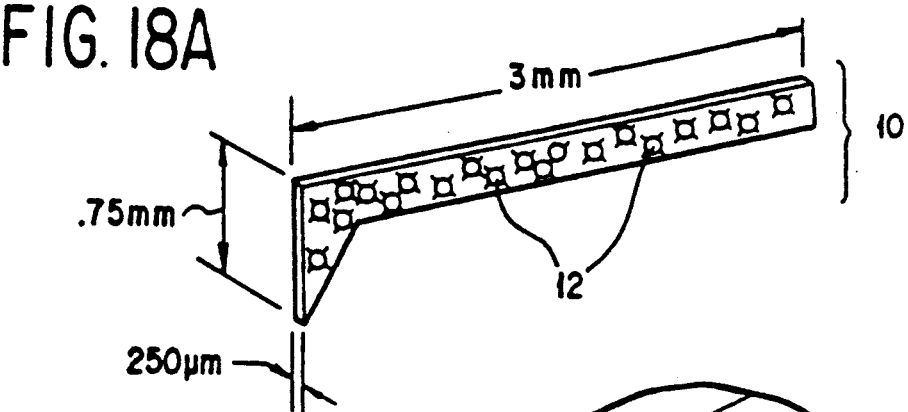
Figure 18B:
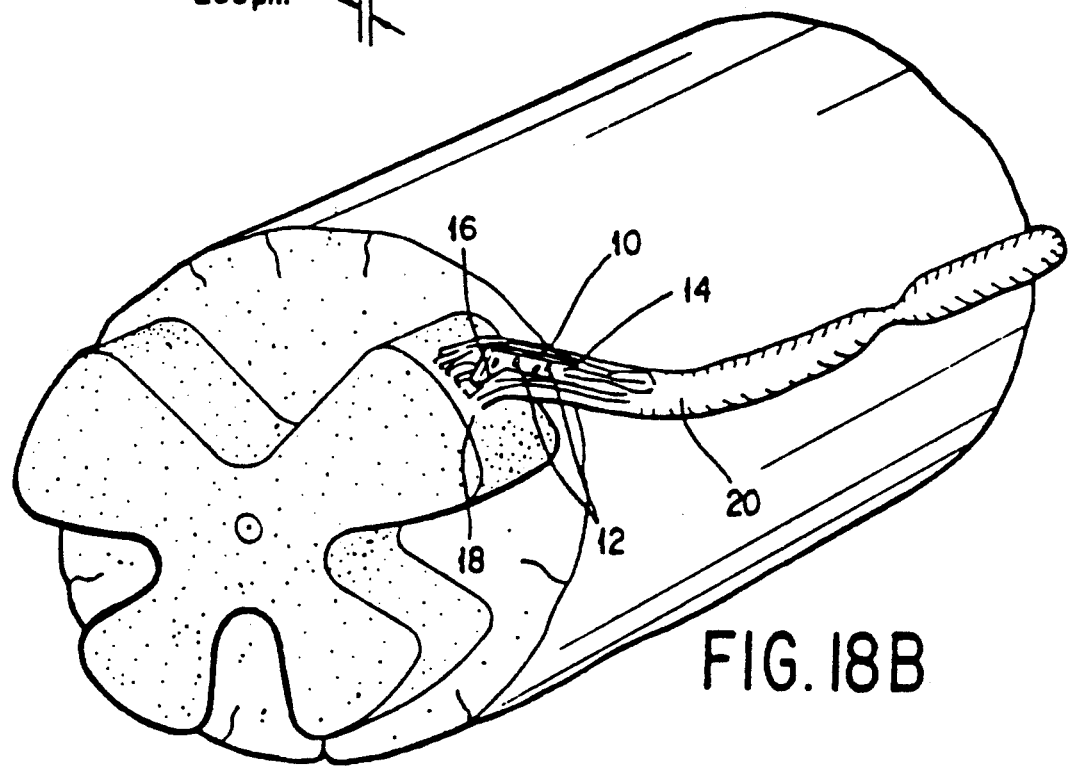
Figure 18C:
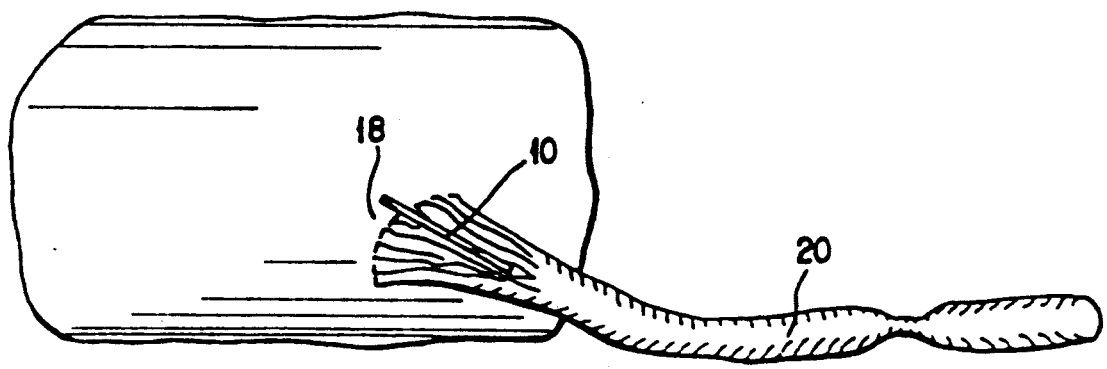

FIGS. 18a, 18b, and 18c are schematic drawings demonstrating the placement of the "pennant-shaped" nitrocellulose implant in the dorsal root entry zone of the spinal cord. FIG. 18a is a frontal view of the "pennant-shaped" nitrocellulose implant (10) containing the activated immature astrocytes (12). FIG. 18b is a cross sectional view of the "pennant-shaped" implant (10) coated with the activated immature astrocytes (12) inserted into the dorsal root cord interface. The pole portion (14) of the pennant protrudes outside the spinal cord (18) into the dorsal root (20) itself, while the broad portion (16) of the pennant-shaped implant lays in the cord (18) proper. FIG. 18c is an overhead view of the "pennant-shaped" implant (10) coated with the activated immature astrocytes inserted into the dorsal root (20) cord (18) interface.

Figure 19A:
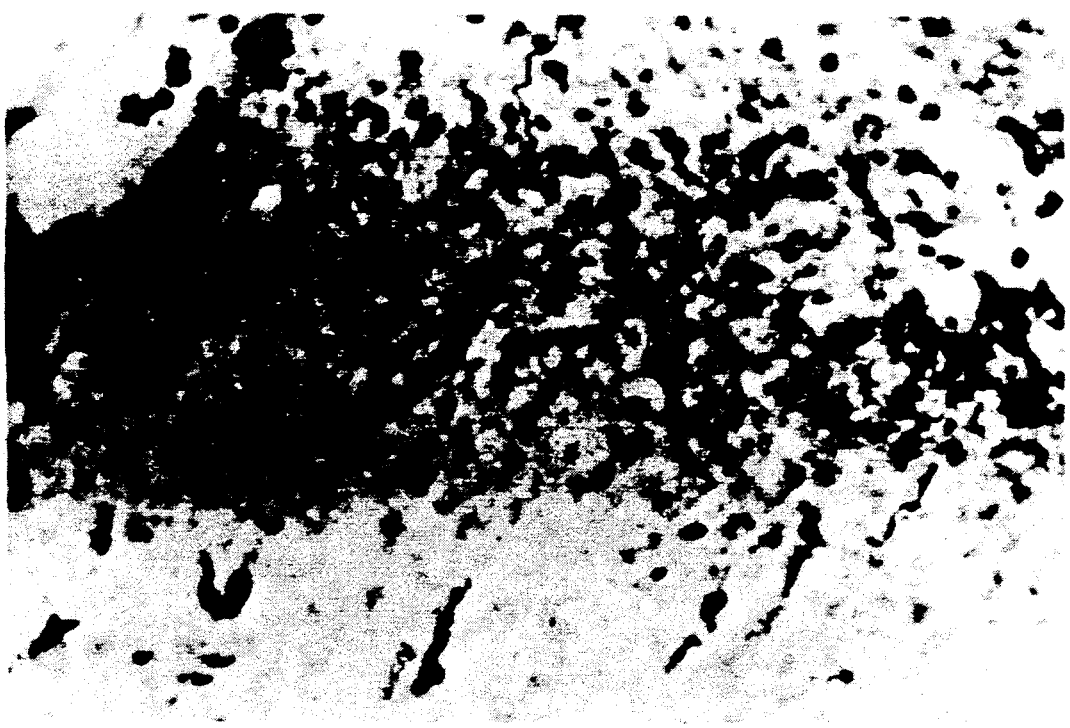
Figure 19B:
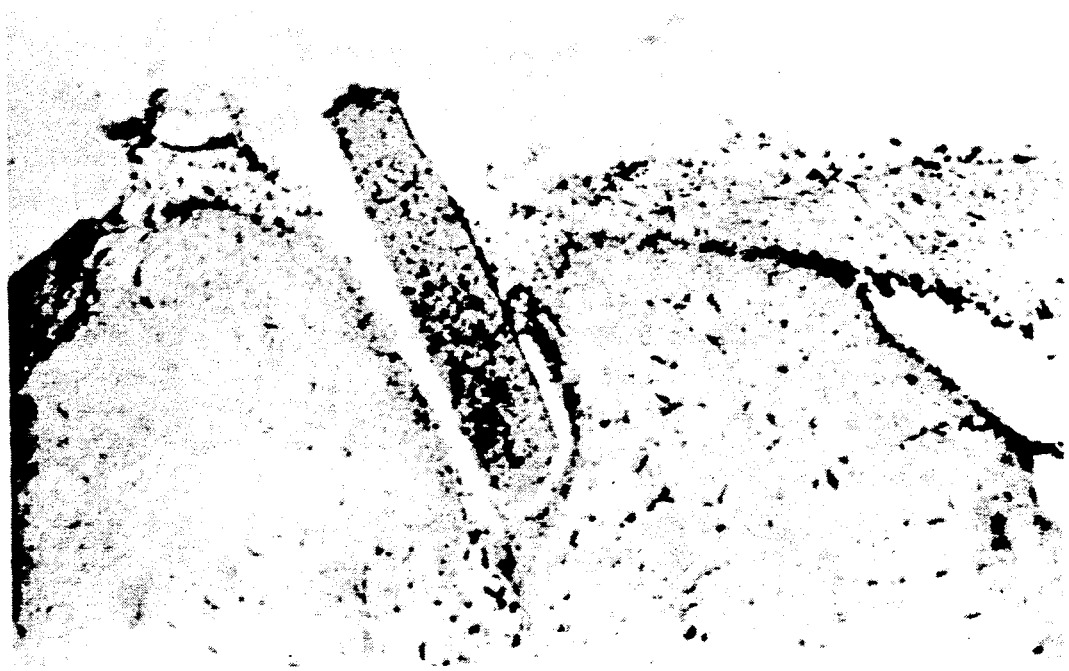
Figure 19C:
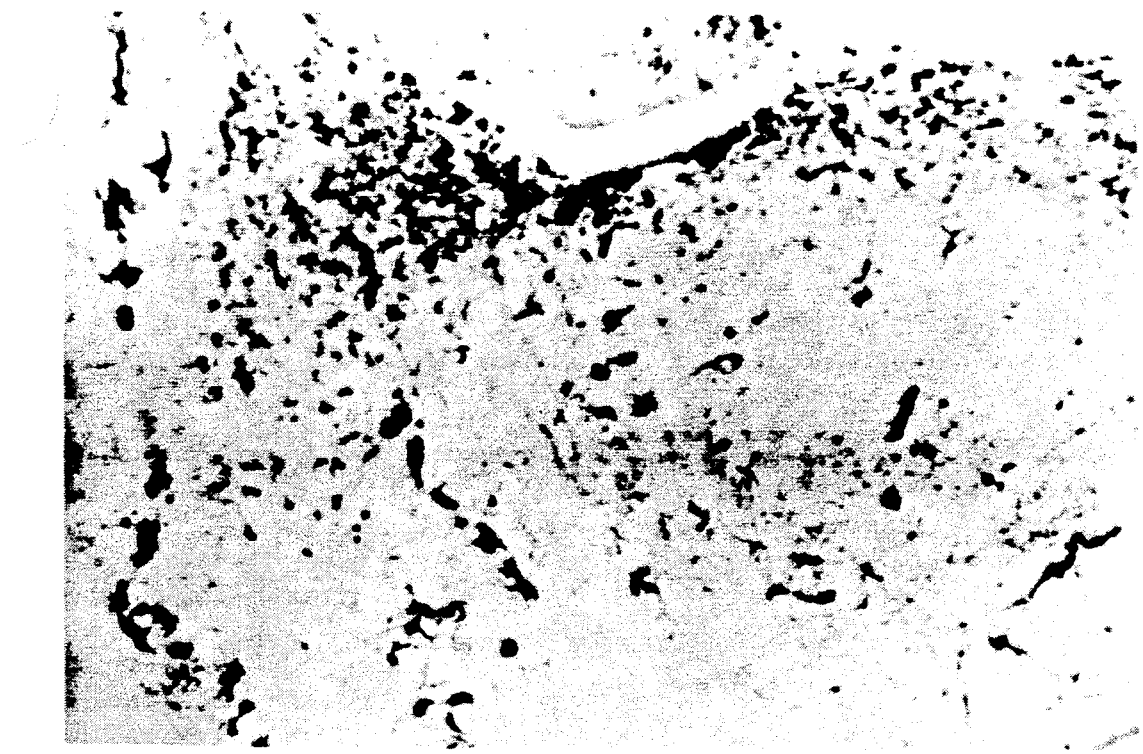
Figure 19D:
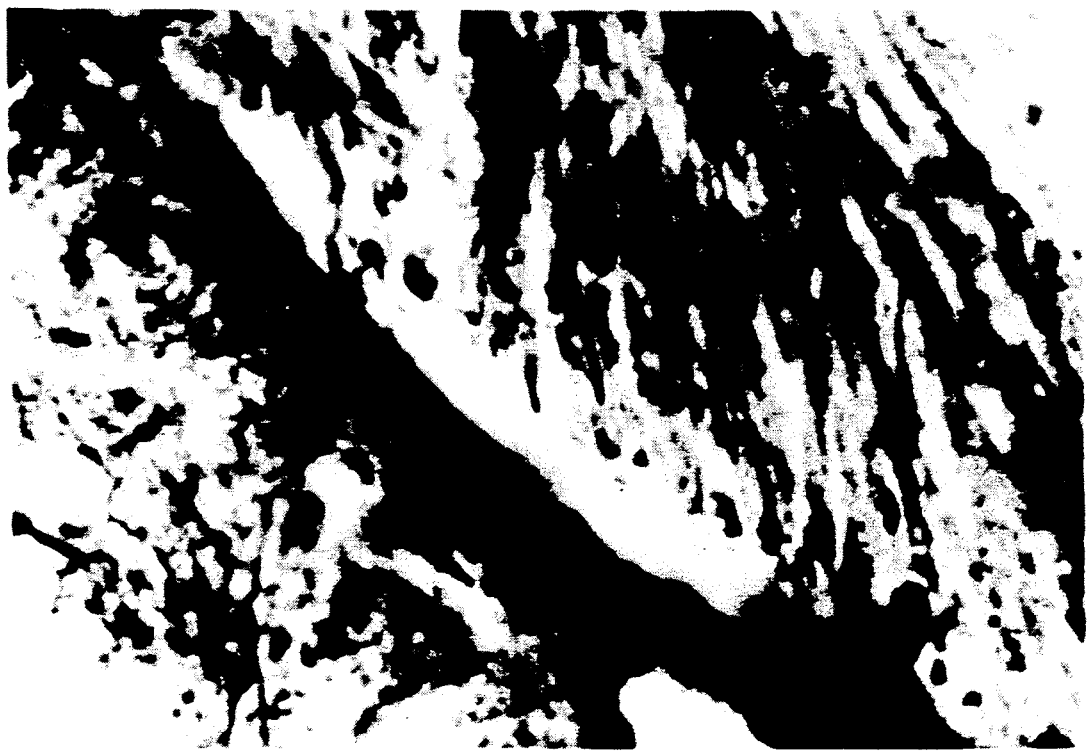

FIGS. 19a, 19b, 19c, and 19d are micrographs showing the placement of the "pennant-shaped" nitrocellulose implant in the L5 dorsal root entry zone of the spinal cord of a 180 day or older rat. FIGS. 19a through 19c indicate that the combination of embryonic astrocytes plus the oriented nitrocellulose implant, represses scar formation locally in the L5 dorsal root entry zone (FIG. 19b) and stimulates axons and blood vessels to enter the central nervous system along the implant surface (FIG. 19b) and stimulate axons and blood vessels to enter the central nervous system along the implant surface (FIGS. 19a and 19c). FIG. 19d demonstrates the normal scar formation which occurs at the dorsal root entry zone of a root-lesioned rat. As indicated in FIG. 19d, when no nitrocellulose implant coated with activated immature astrocytes was inserted in the dorsal root-cord interface, no axonal regeneration was observed. The magnification of the respective FIGURES is as follows: (a) ×400; (b) ×25; (c) ×60; (d) ×400.

FIG. 20. Micrographs of the three morphologically distinct types of E-18 forebrain neurons grown on the surface of immature and mature astrocyte monolayers for 16 hours. a) Neuron lacking any characteristic axon with only multiple short neurites. b) Neuron with one medium length axon-like neurite and multiple short neurites. c) Neuron with one long axon-like neurite and multiple short neurites. All cells were surface labelled with Texas red-conjugated-tetanus toxin C fragment and visualized under rhodamine optics. Scale bar = 10 μm.

FIG. 21. Neurite outgrowth over the surface of either immature (a, c, and e) or mature (b, d, and f) rat forebrain astrocytes. E-18 neurons were grown for 16 hours and then labelled with tetanus toxin C fragment. After fixation in acid alcohol, cultures were labelled with anti-GFAP serum followed by G anti-Rig-FL. The cultures were viewed with (a and b) Rhodamine, (c and d) fluorescein, and (e and f) phase contrast optics. Note that neurite outgrowth is more extensive over the surface of the immature astrocytes than over the surface of the mature astroctes (compare the labelled cells in a and b), and that the immature astrocytes have a more variable expression of GFAP than the mature astrocytes. Scale bar = 20 μm.

Figure 22:
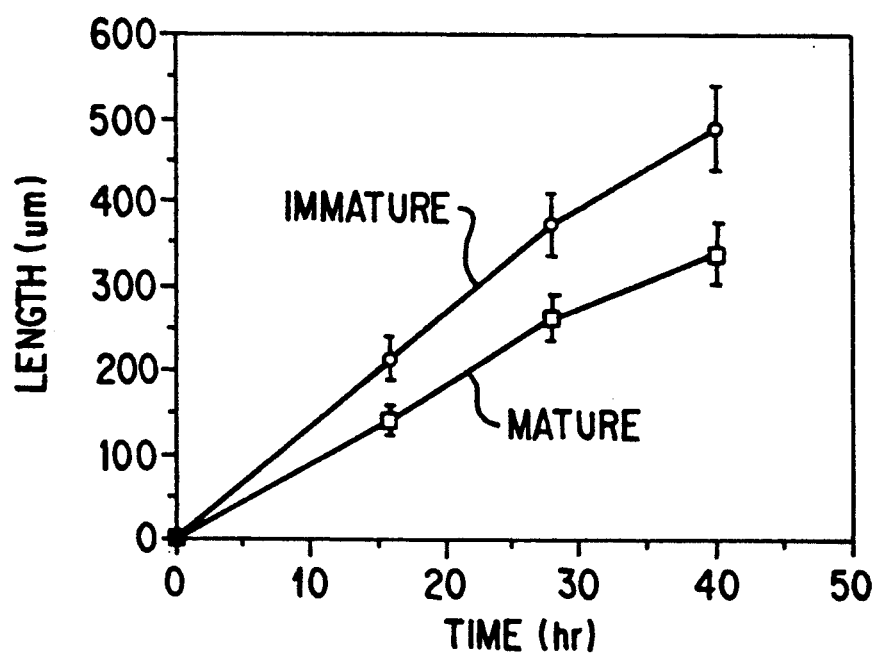
Figure 23B:
Figure 23D:
Figure 23A:
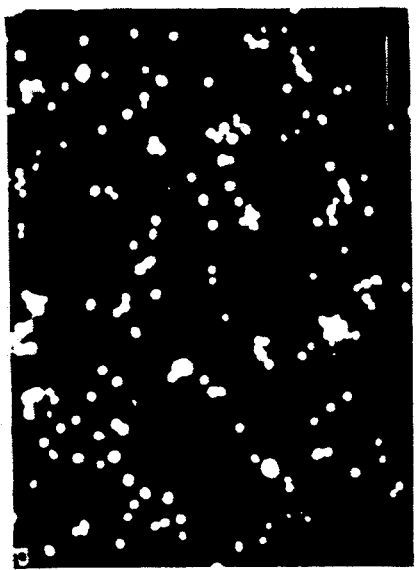
Figure 23C:
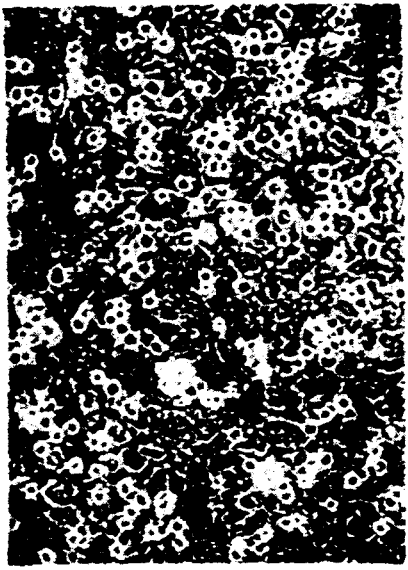

FIG. 22. Neurite outgrowth on immature (closed diamonds) or mature (open squares) astrocytes over different periods of time in culture. Note that in both cases the rate of neurite outgrowth is relatively constant over the time course of the experiment. However, the overall rate of neurite outgrowth is more rapid on immature compared to mature astrocytes.

FIG. 23. Adhesion of E-18 forebrain neurons to the surface of immature (a and c) and mature (b and d) astrocyte cultures. Neurons labelled in suspension with fluorescein diacetate were allowed to adhere to the astrocyte surface for 30 minutes, and non-adherent cells were removed. Cultures were viewed with fluorescein (a and b) or phase contrast optics (c and d). Note that many more neurons adhere to the surface of immature astrocytes than to the surface of mature astrocytes. Scale bar=50 μm.

FIG. 24. Transmission electron micrographs of cultured immature (a and b) and mature (c and d) astrocytes. Note the immature astrocytes (a) are smaller, contain a higher density of organelles but fewer intermediate filaments (b) when compared to mature astrocytes. Scale bar=10 μm in a and c; 1 μm in b and d.

5. DETAILED DESCRIPTION OF THE INVENTION

The present invention is directed to "activated" immature astrocytes, pharmaceutical compositions comprising the same, and methods of utilizing the activated immature astrocytes to treat patients with damage to the nervous system. According to the present invention, it has now been determined that contrary to normal adult astrocytes which promote glial scar formation, certain "critical period" activated immature astrocytes reduce glial scar formation, inhibit extensive bleeding and secondary necrosis, and promote central nervous system axonal regeneration. Thus, the activated immature astrocytes can be administered therapeutically, to promote axon regeneration in the central nervous system, to promote blood vessel regeneration, and/or to reduce glial scar formation and necrosis.

One embodiment of the present invention concerns the use of "activated" immature astrocytes in injectable form or on implants to promote directed axon regeneration and reduce glial scar formation in the forebrain, or in damaged spinal axons of the central nervous system.

The invention is illustrated by way of examples infra, wherein activated immature astrocytes (murine postnatal day 8 or less) were harvested and transplanted into postcritical period animals (postnatal day 14 or more) in order to determine whether an environment conducive for axon regeneration could be re-established in the postcritical animals. The results (discussed in more detail below) indicate that the immature astrocytes survive implantation and reduce the deleterious sequelae of lesions in the brain. In addition, axonal regeneration and/or blood vessel growth was enhanced. The beneficial effects observed included the reduction of necrosis and glial scar formation at the lesion site, as well as the stimulation and promotion of a substratum for the regeneration of postcritical period callosal axons that were not otherwise observed to regenerate. Although the initial studies were performed with activated immature astrocytes (postnatal day 8 or less) harvested on millipore filters placed in the forebrain of postcritical period mice, further examples, presented herein, indicated that the same beneficial effects are observed when the activated immature astrocytes are implanted on polymers in the spinal cord region of paralyzed animals.

In addition, the activated immature astrocytes have been isolated, harvested, and purified in vitro for use in vivo as well as in vitro. In addition, because normal immature astrocytes mature in culture, purified activated immature astrocytes have been genetically engineered to be immortal and forever immature for in vivo therapeutic use. Similarly, the activated immature astrocytes have been used in vitro to promote axon growth in biological cultures.

5.1. ACTIVATED IMMATURE ASTROCYTES

The present invention relates to activated immature astrocytes and the uses thereof to reduce scar formation and promote central nervous system nerve, and/or blood vessel growth or regeneration in areas of nerve damage. The activated immature astrocytes of the invention have the properties of early-stage, immature, astrocytes that have the ability to promote such growth and regeneration and reduce scar formation.

In one embodiment of the invention, such activated immature astrocytes for use in the invention can be identified by observing their ability, when seeded onto a suitable polymer implant and introduced in vivo, to promote nerve regeneration (see Sections 6, 7, infra).

In another embodiment, activated immature astrocytes can be identified for use by observing their ability, in vitro, to support increased CNS neurite outgrowth or neuronal adhesion relative to mature (e.g., isolated from an adult, or aged in vitro) astrocytes. As an example, assays such as those described in Section 9, infra, can be used.

In yet another embodiment, activated immature astrocytes can be identified morphologically. Activated immature astrocytes include but are not limited to those with a polygonal, epithelioid, or stellate, rather than flat, morphology. In addition, an abundance of condensed heterochromatin in the nucleus, and a dense cytoplasm containing many closely packed organelles, few dense bodies, and small numbers of intermediate filaments are characteristic of some activated astrocytes. In addition, activated immature astrocytes are usually small, with few junctional specializations, and a small cytoplasm to nucleus ratio. In contrast, mature astrocytes often have a less dense cytoplasm with less closely packed organelles, but many dense bodies and large numbers of intermediate filaments. Mature astrocytes also tend to be large cells, with little condensed chromatin and an increase in both size and cytoplasm to nuclear ratio, in close apposition with one another, and containing many junctional specializations between them. The above description is not meant to limit the invention, but rather, to provide a method for use in a specific embodiment of identifying a subset of activated immature astrocytes by virtue of their morphological characteristics.

The activated immature astrocytes of the invention are those astrocytes having properties associated with a critical period of development in the host from which they are derived. In one embodiment, such a critical time period can be identified as the time prior to full development of the neural pathways in a given region in the embryo or neonate. For example, in a specific embodiment in which it is desired to promote nerve regeneration in a specific region of the central nervous system, activated immature astrocytes for use can be selected by obtaining those astrocytes corresponding to a time period prior to the full development of the neural pathways in such specific region. For example, it is expected that the critical period for use in promoting regeneration and reducing scar formation in the area of the corpus callosum in the forebrain will end at a later stage than such critical period for use in the spinal cord, since the corpus callosum finishes developing at a later time than the neural pathways of the spinal cord. The time periods for neural pathway development are known in the art (see, e.g., Silver et al., 1982, J. Comp. Neurol. 210:10 (for rodent); Warkany, J., 1971, *Congenital Malformations*, Yearbook Medical Publishers, Inc., Chicago, Ill., pp. 189-295 (for human); Hamilton, W. J., et al., 1972, *Hamilton, Boyd and Mossman's Human Embryology; Prenatal Development of Form and Function*, Heffer, Cambridge (for human)). Astrocytes selected for use in the present invention, initially derived from host organisms before completion of neural pathway development, may be tested for their activity in promoting CNS nerve regeneration and reducing scar formation by in vitro and/or in vivo assays as described infra in Sections 6-9. The astrocytes can be purified by standard procedures known in the art (see, e.g., Sections 7.1.1 and 9.1.1, infra).

In an embodiment in which murine astrocytes are used, the activated immature astrocytes of the invention consist of those astrocytes of about postnatal day 8 or less.

In an embodiment directed to the use of human activated immature astrocytes, such activated astrocytes can be obtained from the human embryo, and in a preferred embodiment, from embryos of the first trimester of pregnancy. For example, such astrocytes may be obtained from aborted fetuses, cryopreserved samples or immortalized cell lines derived therefrom, etc.

In another embodiment directed to the use of human activated immature astrocytes, such astrocytes/glial cells can be obtained from the olfactory bulb of human embryos, children or adults. Such olfactory bulb glial cells have the unique property, corresponding to "critical period" astrocytes from other regions of the central nervous system, of being capable of producing an especially favorable axon growth-promoting surface. These olfactory bulb glial cells can be obtained during standard neurosurgical procedures; for example, cells of the olfactory bulb are often removed in part during certain operations such as the clipping of an anterior communicating artery aneurism (see, e.g., Neurosurgery, 1984, Wilkins and Rengachary, eds., McGraw Hill). In a preferred embodiment, olfactory bulb ensheathing cells can be used.

Activated immature astrocytes for use in the present invention may be obtained directly from the host organism within the critical time periods. Alternatively, other sources of such activated astrocytes include but are not limited to immortalized activated astrocyte cell lines and/or cryopreserved samples containing activated immature astrocytes.

For example, activated immature astrocytes may be immortalized by procedures known in the art, so as to preserve sources of such astrocytes for future use. Immortalized astrocytes can be maintained in vitro indefinitely. Various methods of immortalization are known in the art and can be used in the practice of the instant invention, including but not limited to viral transformation (e.g., with SV40, polyoma, RNA or DNA tumor viruses, Epstein Barr Virus, bovine papilloma virus, or a gene product thereof), chemical mutagenesis, etc. In preferred embodiments, the cell line is immortalized by a virus defective in replication, or is immortalized solely by expression of a transforming virus gene product. For example, activated immature astrocytes can be transformed by recombinant expression vectors which provide for the expression of a replication-defective transforming virus or gene product thereof. Such procedures are known in the art.

As mentioned supra, in an alternative embodiment, activated immature astrocytes can be cryopreserved for use at some future time. Various methods for cryopreservation of viable cells are known and can be used (see, e.g., Mazur, 1977, cyrobiology 14:251-272; Livesey and Linner, 1987, Nature 327:255; Linner, J. G., et al., 1986, J. Histochem. Cytochem. 34(9):1123-1135; U.S. Pat. No. 4,199,022 by Senkan et al.; U.S. Pat. No. 3,753,357 by Schwartz; U.S. Pat. No. 4,559,298 by Fahy).

In a preferred aspect of cryopreservation, cryoprotective agents, a controlled freezing rate, and storage at a low temperature such as that of liquid nitrogen ($-196°$ C.) can be used. Cryoprotective agents which can be used include but are not limited to dimethyl sulfoxide (DMSO) (Lovelock, J. E. and Bishop, M. W. H., 1959, Nature 183:1394-1395; Ashwood-Smith, M. J., 1961, Nature 190:1204-1205), glycerol, polyvinylpyrrolidine (Rinfret, A. P., 1960, Ann. N.Y. Acad. Sci. 85:576), polyethylene glycol (Sloviter, H. A. and Ravdin, R. G., 1962, Nature 196:548), albumin, dextran, sucrose, ethylene glycol, ierythritol, D-ribitol, D-mannitol (Rowe, A. W., et al., 1962, Fed. Proc. 21:157), D-sorbitol, i-inositol, D-lactose choline chloride (Bender, M. A., et al., 1960, J. Appl. Physiol. 15:520), amino acids (Phan The Tran and Bender, M. A., 1960, Exp. Cell Res. 20:651), methanol, acetamide, glycerol monoacetate (Lovelock, J. E., 1954, Biochem. J. 56:265), and inorganic salts (Phan The Tran and Bender, M. A., 1960, Proc. Soc. Exp. Biol. Med. 104:388; Phan The Tran and Bender, M. A., 1961, in Radiobiology, Proceedings of the Third Australian Conference on Radiobiology, Ilbery, P. L. T., ed., Butterworth, London, p. 59).

A controlled slow cooling rate is preferred. Different cryoprotective agents (Rapatz, G., et al., 1968, Cryobiology 5(12):18-25) and different cell types have different optimal cooling rates (see e.g., Rowe, A. W. and Rinfret, A. P. 1962, Blood 20:636; Rowe, A. W., 1966, Cryobiology 3(1):12-18; Lewis, J. P., et al., 1967, Transfusion 7(1):17-32; Mazur, P., 1970, Science 168:939-949 for effects of cooling velocity). A programmable freezing apparatus, as one example, can be used.

Cryopreserved astrocytes are preferably thawed quickly (e.g., in a 37° C. waterbath) before use according to the present invention in the promotion of nerve and blood vessel regeneration and/or reduction of scar formation.

5.2. Methods of Using Activated Immature Astrocytes in the Promotion of Nerve or Blood Vessel Regeneration and/or Scar Reduction

5.2.1. Treatment of Nerve Injury and Disorders

Activated immature astrocytes can be used in accordance with the present invention to treat subjects in which it is desired to promote CNS nerve or blood vessel regeneration and/or reduce scar formation. Thus, activated immature astrocytes can be applied, in any of various formulations as described infra, to areas of nerve damage. The activated immature astrocytes can be administered to patients in whom the nervous system has been damaged by trauma, surgery, ischemia, infection, metabolic disease, nutritional deficiency, malignancy, toxic agents, paraneoplastic syndromes, degenerative disorders of the nervous system, etc. Examples of such disorders include, but are not limited to, Alzheimer's Disease, Parkinson's Disease, Huntington's chorea, amyotrophic lateral sclerosis, progressive supranuclear palsy, and peripheral neuropathies. In another embodiment, activated immature astrocytes can be applied to a wound to reduce scar formation. As one example, after an operation, activated astrocytes can be applied according to the present invention in order to reduce scar formation from lesions due e.g., to arteriovenous malformation, necrosis, bleeding, craniotomy, which can secondarily give rise to epilepsy. In another embodiment of the invention, activated immature astrocytes can be used for treatment of epilepsy, by stabilizing the epileptic focus and reducing scar formation.

In a preferred embodiment of the invention, astrocytes for use in promoting nerve/blood vessel regeneration or reducing scar formation in a region of the CNS are initially derived from that region. For example, it is preferred to use activated immature astrocytes of the forebrain for treatment of a forebrain lesion, activated immature astrocytes of the spinal cord for treatment of a spinal cord lesion, and so on. However, astrocytes from regions other than the site of application can also be used.

Autologous transplants of activated immature astrocytes (i.e., the use of astrocytes derived from the same host) are preferred. However, allogeneic and even xenogeneic astrocyte transplants may be used in the practice of the present invention. If cross-species transplants are used, closely related species are preferred. In cross-species transplants in which immunologic rejection is likely, such rejection may be reduced or prevented by means known in the art, i.e., immunosuppressive conditioning regimens including but not limited to chemotherapy (e.g., cyclophosphamide) and irradiation (see, e.g., Gluckman, E., et al., 1984, in Aplastic Anemia, Stem Cell Biology and Advances in Treatment, Young, N. S., et al., eds., Alan R. Liss, Inc., N.Y., pp. 325-333).

5.2.2. Pharmaceutical Compositions

The present invention also provides pharmaceutical compositions which comprise an effective amount of the activated immature astrocytes, and a pharmaceutically acceptable carrier. Such pharmaceutically acceptable carriers include sterile biocompatible pharmaceutical carriers, including, but not limited to, saline, buffered saline, dextrose, and water.

5.2.3. Modes of Delivery

There is a wide range of methods which can be used to deliver the activated immature astrocytes of the invention for use in the promotion of CNS nerve or blood vessel regeneration and/or scar reduction.

In one embodiment of the invention, the activated immature astrocytes can be delivered by direct application, for example, direct injection of a sample of activated astrocytes into the site of nerve damage. In a particular embodiment, such astrocytes can be purified, for example, they can be cell line astrocytes or astrocytes purified from a tissue sample.

In a specific embodiment, the activated immature astrocytes can be delivered in a media which partially impedes their mobility so as to localize the astrocytes to a site of nerve damage. For example, activated astrocytes can be delivered in a paste or gel, e.g., a biodegradable gel-like polymer (e.g., fibrin, a hydrogel, etc.), or even contained in an embryonic tissue section placed at the site of nerve damage. Such a semi-solid media would also have the advantage that it would impede the migration of (scar-producing) undesirable mesenchymal components such as fibroblasts into the site.

Other methods of using and applying activated immature astrocytes of the invention include but are not limited to the use of polymer implants and surgical bypass techniques. Such methods may be used together, alone, or in conjunction with other methods as described supra. Uses of polymer implants and surgical techniques are described in more detail infra.

5.2.3.1. The Use of Polymer Implants

In a preferred embodiment of the invention, activated immature astrocytes can be applied to a site of nerve injury in a form in which the astrocytes are seeded or coated onto a polymer implant. An astrocyte-containing composition may be applied to the implant in vitro, or alternatively, implants may be coated with astrocytes in vivo by surgical insertion into a host younger than "critical period" age.

Various types of polymer implants can be used in this embodiment of the invention, with various compositions, pore sizes, and geometries. Such polymers include but are not limited to those made of nitrocellulose, polyanhydrides, and acrylic polymers (see e.g., those described in European Patent Publication No. 286284, published Oct. 12, 1988, by Valentini et al.; Aebischer, P., et al., 1988, Brain Res. 454:179-187; Aebischar, P., et al., 1988, Prog. Brain Res. 78:599-603; Winn, S. R., et al., 1989, Exp. Neurol. 105:244-250). In a preferred embodiment, nitrocellulose is used.

The pore size of such implants are preferably about 0.45 $\mu$m or greater. Too small a pore size can cause activated astrocytes to flatten and lose their "activated" character (see Section 6.2.5, infra).

Various geometries of polymer implants are envisioned for use; in a preferred embodiment, polymer implant shapes can be selected which tend to "mimic" the trajectory of the nerve pathway over which it is desired to promote nerve regeneration. For example, as described infra in the examples sections, a pennant-shaped implant can be used to promote regeneration into the spinal cord dorsal root entry zone. Similarly, a "home-plate" shaped implant can be used in promoting nerve regeneration in the corpus callosum. Various other geometries are within the scope of the invention and may be used.

In another embodiment of the invention, polymers can be used as synthetic bridges, over which nerve regeneration can be promoted and scar formation can be reduced by application of activated immature astrocytes to the end(s), or in the vicinity of, the bridge. For example, an acrylic polymer tube with activated immature astrocytes at one or more ends, or throughout the tube, can be used to bridge lesions rostrally or bypass lesions, e.g., of the spinal cord, over which nerve regeneration can be induced. In a preferred embodiment, semi-permeable tubes may be used, e.g., in the dorsal columns or dorsal afferents, which tubes can contain and provide for the release of trophic factors or anti-inflammatory agents. The types of tubes which can be used include but are not limited to those described in various publications (see, e.g., European Patent Publication No. 286284, published Oct. 12, 1988, by Valentini et al; Aebischer, P. et al., 1988, Brain Res. 454:179-187; Aebischer, P., et al., 1988, Prog. Brain Res. 78:599-603; Winn, S. R., et al., 1989, Exp. Neurol. 105:244-250).

5.2.3.2. The Use of Actiated Astrocytes in Conjunction with Surgical Bypass Techniques In another specific embodiment of the invention, the use of activated immature astrocytes is combined with surgical bypass techniques to promote nerve or blood vessel regeneration or to reduce scar formation in a given region.

In particular, surgical procedures which move a potentially regenerating fiber away from white matter and closer to its target grey matter can be used. Such procedures would tend to minimize the potential inhibitory influence of white matter (Caroni and Schwab, 1988, J. Cell Biol. 106:1281-1288; Caroni and Schwab, 1988, Neuron 1:85-96) on nerve regeneration. As one example, a cut dorsal root can be surgically implanted back into the spinal cord just lateral to its normal point of entry (i.e., the DREZ), so as to place the sensory fibers in closer proximity to their target, the grey matter of the dorsal horn, and minimize the inhibitory influence of nearby white matter structures such as the dorsal columns. The concurrent or subsequent provision of activated immature astrocytes (e.g., on a polymer implant) can then be used to induce axonal regeneration into the grey matter. Such a procedure is described by way of example in Section 11, infra.

In another embodiment of the invention, the use of activated immature astrocytes can be combined with surgical procedures for bridging and thus bypassing a CNS lesion. In one embodiment, the lesion can be a spinal cord lesion. If the spinal cord is completely injured at a particular level, then neural signals can neither ascend nor descend beyond this point. If an embodiment in which regeneration of the spinal sensory roots which enter the cord below the level of the lesion is desired, these roots may be cut and rerouted to a new level of the spinal cord above the lesion. Since these roots must now travel a distance greater than they normally do, a "bridging" substrate for this additional growth is desired; such bridging substrates may be synthetic or natural, including but not limited to polymer tubes and autologous nerve grafts. For example, a nitrocellulose tube or an autologous peripheral nerve may be implanted to function as a bridge. Although regenerating nerves will readily grow on substrates such as polymer tubes or autologous nerve grafts, such nerves usually reenter the CNS only to a very limited extent. In order to promote their reentry into the CNS, activated immature astrocytes can be provided, in combination with such surgical techiques, in accordance with the present invention.

6. EXAMPLE: ACTIVATED IMMATURE ASTROCYTES PROMOTE NEURAL AND BLOOD VESSEL REGENERATION AND REDUCE SCAR FORMATION IN THE FOREBRAIN

6.1. Materials and Methods

6 1.1. Transplantation of Implants and Cellular Coatings

6.1.1.1. Insertion of the Implants

Timed pregnant C57 BL/6J mice were obtained from the Jackson Laboratories, Bar Harbor, Me. The glial "sling", which forms the transient axon guidance pathway between the right and left cortical hemispheres of the brain, of 16 day embryos (E16) of timed pregnant mice (Silver, et al., supra 1982) was lesioned by inserting a microneedle into the embryos' calvarium approximately 1 mm rostral to the cranial landmark "lambda" to a depth of about 2 mm. As a result of the above process, the lesioned mice were consistently acallosal. In an experiment to test the efficiency of the technique, 50 animals were acallosal out of the 50 lesioned.

The lesioned embryos, once born, were then anesthetized and implanted with a specially designed piece of nitrocellulose filter (a 1-mm$^2$, "home-plate" shaped piece of cellulose membrane filter (Millipore), 0.45-$\mu$m pore size) on postnatal day (P) 2, 5, 8, 14, and 21 and at 8 months. In the neonates, the skull was still pliable and did not require drilling. An incision through the skin and cranium was made horizontally between the eyes and the skin was retracted. The surface of the skull was scraped free of tissue in order to minimize contamination of other cell types onto the implant as it was inserted. The specially designed implant was then inserted, pointed side first, 2-5 mm into the stab wound. The animals were then maintained in a normal growth environment for 2 or more days.

In addition, in order to determine whether a change in "activated" astrocyte morphology from stellate (i.e. inserted) to flat altered the efficiency of the astrocytes to provide a conducive substratum for axon elongation, a second set of experiments were conducted wherein portions of the implants were precrushed midsagitally to reduce pore size before insertion into the neonatal brain according to the above process.

6.1.1.2. Removal of the Implants Plus Their Cellular Coatings

The implants, plus their cellular coatings, were removed from the decapitated acallosal mice 48 hours after implantation on postnatal day 2 (P2). The tissue around the implant was carefully dissected and the implant was removed with forceps which prevent the cells on the surface from being crushed or stripped away. The implants, and their cellular coatings, were then dipped in N-2 medium (Bottenstein, J. E. and Sato, G. H., 1983, Proc. Natl. Acad. Sci. U.S.A. 79:514-517) and placed in a humid chamber at 37° C. until they were transplanted a few minutes later.

6.1.1.3. Transplantation of the Implants and Their Cellular Coatings to Older Postcritical Period Hosts Host C57 BL/6J mice (at postnatal day 17, 34 or 8 months) obtained from Jackson Laboratories, Bar Harbor Me., were made acallosal in the embryo or on the day of birth. The transplants (i.e. the implants plus their cellular coatings) were inserted in the same manner as described above.

The animals were then killed 0.5, 1, 2, 3, 5, 6, and 7 days and 2 months after implantation by perfusion through the heart. The perfusion was performed in two steps: first, 2-5 ml of an 0.15 M phosphate buffer solution at 37° C. was injected into the left ventricle, followed by fixative (0.5% glutaraldehyde/2.0% formaldehyde in the same buffer, with 0.5% dimethyl sulfoxide (DMSO). The brains were quickly dissected from the cranium and placed in the same fixative overnight at 4° C. The filter and surrounding tissue were subsequently embedded in Spurr's plastic using standard procedures. Serial 1 $\mu$m sections were taken through the implant and stained with toluidine blue. Certain regions were sectioned ultra-thin, stained with uranyl acetate and lead citrate, and viewed with a Zeiss 109 electron microscope. For specimens examined by a scanning electron microscope (SEM), the tissue above the implant was gently dissected away and the specimens were osmicated and dehydrated through a graded series of alcohols. The samples were critical-point dried in a Balzers CPD 020 and sputtercoated with gold with an Edwards E306 device. After being mounted on aluminum stubs, they were viewed with an Etech scanning electron microscope.

6.1.2. Immunohistochemistry

Variously aged postnatal C57 BL/6J mice made surgically acallosal and containing implants for one week were anesthetized and perfused through the heart with 2-5 ml of 4.0% formaldehyde in phosphate buffered saline (PBS, pH 7.5). The brains were dissected from their calvaria and immersed in fixative for 2 hours, then cyroprotected by using a graded series of sucrose PBS solutions (10% sucrose, PBS solution for 30 minutes, 15% for 30 minutes and 20% for 2 hours to overnight); 10-μm sections were taken on a Slee HR Mark II cryostat microtome.

Polyclonal antibodies against purified laminin and fibronectin were received from Dr. G. Martin (NIH). The sera were used at dilutions of 1:50. Antibodies against glial fibrillary acidic protein (GFAP) were provided by Dr. Robert Miller (Case Western Reserve, Cleveland, Ohio). They were diluted 1:1,000 and applied for 1 hour at room temperature. Sections were rinsed in PBS (3-15 minute washes) and incubated with peroxidase conjugated goat anti-rabbit IgG (Cooper Biomedical, Malvern, Pa.) at a dilution of 1:100 for 30 minutes at room temperature or goat anti-rabbit FITC (fluorescein isothiocyanate) at a dilution of 1:50 for 1 hour. Sections were rinsed again in PBS, and peroxidase conjugates were incubated in a solution containing 15 mg DAB (3,3 diaminobenzidine tetrahydrochloride; Eastman Kodak Co., Rochester, N.Y.) per 100 ml Tris (pH 7.5) for 30-45 minutes at room temperature in the dark.

6.1.3. Horseradish Peroxidase Injections

In order to determine the location of cell bodies that contribute axons to the implant surface, acallosal mice implanted on postnatal day 5 (P5) and allowed to survive 5 weeks were given a single, small wedge of crystalline horseradish peroxidase (Sigma VI) that was inserted (with a spinal needle) very superficially into the cortex of one hemisphere of the brain in a region immediately lateral to the implant. On the following day, the animals were killed and perfused with 0.5% glutaraldehyde and 2% formaldehyde in 0.15 M PBS. Brains were removed and placed in the same fixative for 4 hours. Sections were cut on a vibratome at 65 μm and incubated in 50 mg of DAB in 100 ml Tris buffer (pH 7.5) for 20 minutes. A solution of 0.6% hydrogen peroxide was added and the sections were incubated 15-20 minutes longer. Sections were counterstained with neutral red and mounted on the slides.

6.1.4. 3H-Thymidine Autoradiography of Transplants

Acallosal neonates, implanted with filters on postnatal day 2 (P2), were injected intraperitoneally with $^3$H-thymidine (5 μCi/g of body weight) at 6, 18, and 30 hours after implantation. Implants were removed 18 hours after the last injection and transplanted into postnatal day 23 (P23) surgically induced acallosal mice obtained from Jackson Laboratories. The mice were perfused 4 days after transplantation and prepared for plastic embedding. Sections 1 μm thick were mounted on slides and coated with Kodak NTB-2 autoradiographic emulsion. The coated slides were placed in light-proof containers and stored at −5° C. for 6 weeks. Slides were processed for photography at 18° C.

6.2. Results

6.2.1. Determination of the "Critical Period" in Astrocytes for Axon Elongation An analysis of the scanning electron micrographs of the acallosal mice implanted with untreated nitrocellulose bridges at various stages (P2, 5, 8, 14, and 21, and 8 months) indicated that the glial response at 24-48 hours after implantation produced a terrain along the filter that was suitable for axon extension only in animals that were implanted before or on postnatal day 8 (P8). This was shown by the presence of many unmyelinated axons interspersed among the attached glial cells (astrocytes). See FIGS. 1 and 16. The micrographs indicated that glia in the P2 and P8 implants coated the majority of the implant surface, providing a substrate on to which axons and blood vessels were extended (FIGS. 4a through 4c). In P2 and P8 implants, the glia (astrocytes) on the filter appeared to be stellate in shape and respond to the presence of axons by sending out many cytoplasmic extensions around the fibers. See FIG. 1d.

However, the CNS glial response generated by implantation of animals on or later than postnatal day 14 (P14) did not produce a terrain readily suitable for axon extension. The glia in the P14 animals appeared to be flat and lacked extensive infiltration of processes. The 27 animals given naked, untreated implants postnatally at 2 and 3 weeks and 8 months showed little or no growth of axons on to the implant when examined at 1 week and as late as 2 months after implantation (see FIG. 2).

6.2.2. Determination of the Location of the Cell Bodies That Contributed Axons to the Implant Surface A review of the micrographs concerning the horseradish peroxidase injections indicated that the representative sections contained retrogradely labeled cortical neurons in a position contralateral and homotopic to that of the injection site (see FIG. 3). Thus, the results demonstrated that some of the commissured axons emerged from one region of the brain and grew across the midline to the opposite region of the brain, using the implant as a pathway.

6.2.3. Host Glial Response to Nitrocellulose Bridges Implanted at Various Postnatal Ages Implantation of acallosal mice at various stages was done not only to evaluate the ability of the glial coating to provide an adequate substratum for axonal elongation but also to compare age-related changes in the host gliotic response. The micrographs showed that when implants were placed within the presumptive callosal pathway of acallosal mice at P2 and P8, the glial cells rapidly migrated onto the surface of the filter during the first 12-24 hours after implantation (See FIG. 4). The glial cells attached themselves to the implant by extending their cytoplasmic processes deep into the implant's 0.45 μm pores.

The identification of the glial elements on the filter as astrocytes, as well as the extensive branching of their processes into both the prosthesis and encompassing tissue, were dramatically shown in the GFAP-stained sections (see FIG. 5). In P2 implants there were only a few macrophages around the filter 48 hours after implantation and there was no evidence of tissue necrosis or persistent bleeding (see FIG. 4).

In addition, the GFAP results demonstrated that the rapidity of astrocyte movement onto the filter and attachment with the filter decreased gradually as the age of implantation increased. In P8 implants examined after 48 hours, many GFAP-positive glia were already attached.

In contrast to P2 and P8 neonates, animals implanted on P14 and P21 showed only slight glial activity after implantation. Filters examined at this stage were coated mainly with degenerating tissue and vascular elements. Thus, the reaction and migration of glia onto the filter in animals implanted on or later than P14 required a longer period of time, often taking a full week for cells to reach the vicinity of the filter.

Moreover, the reactive older astrocytes had a conspicuous change in shape from stellate (i.e. inserted) to flat (compare FIG. 2a with FIG. 2e; also FIG. 5a with FIG. 5b). Macrophages with inclusions, mesenchymal tissues, and large amounts of necrotic debris always persisted within these developing scars. Another significant variation of the host glial reaction in older animals was the relative inability of the mature form of reactive astrocyte to insert processes into the implant. Filters introduced intracerebrally at later stages (P21 and 8 months), and examined after 7 days, had limited penetration of glial processes into their pores (FIG. 2). Rather than inserting, the glia flattened on the surface of the filter and encapsulated the prosthesis by forming sheets several cell layers thick.

The anti-GFAP staining pattern at P21 showed sheets of flattened astrocytes having only a few short processes penetrating into the implant (FIG. 5). These flattened astrocytes were often surrounded by nonstaining arachnoidal cells that composed a much larger proportion of the cell population encompassing the implant than at earlier stages.

6.2.4. Extracellular Matrices Associated with Gliotic Response at Different Ages The gliotic reaction that appeared 2-7 days after implantation in P2 neonates did not stimulate the production of collegen fibers or basal laminae within the parenchyma of the CNS. Only basal laminae that normally occur around capillaries and at the pial surface could be found. However, when animals implanted at P2 were examined for laminin (a major protein component of basal lamina), an unusual staining pattern was revealed. As expected, laminin appeared to be concentrated in the basal laminae of the blood vessels and the pia mater throughout the brain. However, laminin was also found within the pores of the filter in regions containing inserted glial processes, sites having no observable amounts of basal lamina (compare FIGS. 6a, 6b with 6c, 6d), as well as in collagen associated with glial scar. Ectopic basal laminae first appeared in small, isolated patches among cells surrounding the implant in some P8 individuals examined after 2-7 days. Interestingly, in P8 animals, axons were not observed juxtaposed to the ectopic basal lamina. However, axons were observed clustered along the plasma membrane of astrocytes less than 10 μm away from the basal lamina (FIGS. 7b-d). The anti-laminin staining within the pores of the filter was greatly reduced or absent in brains implanted on or later than P14 (FIG. 6d). Collagen fibers were seen throughout the scar, occupying spaces between cells and cell layers. Transmission electron microscope (TEM) examination of the banding pattern for the fibers identified them as being composed of type I collagen.

6.2.5. Axon Reaction to Flattened Astrocytes in Postnatal Day 2 Neonates Induced by Compressing the Pores of the Implant Observation of the scanning electron micrographs taken 48 hours after the insertion of crushed implants on postnatal day 2, indicated that many of the GFAP-positive astrocytes in the crushed region spread out to become flat and often formed a confluent monolayer. In contrast, the astrocytes that accumulated in layers over the uncrushed region of the implant were stellate with many ruffles, blebs, and cytoplasmic extensions (see FIG. 8).

In addition, the micrographs indicated that the growing axons extended over the "activated" stellate-shaped astrocytes infiltrating the porous portion of the implant but did not grow among the flattened astrocytes on the crushed portion (see FIG. 17). This experiment also demonstrated the importance of a proper pore size in the polymer for maintaining the astrocyte in an "activated" form when it is transplanted on nitrocellulose.

6.2.6. Transplantation of Glial-Coated Implants from Neonatal to Postcritical Period Animals An analysis of coronal sections of postcritical period animals (i.e. P14 or greater) that received transplanted filters precoated with glia from neonates that were injected with $^3$H-thymidine indicated that many of the inserted glia were indeed transferred and survived transplantation (see FIG. 9). Silver grains were observed not only above glia attached to the filter but also above those along blood vessels which were well away from the surface of the implant. Thus, transplanted glia can migrate from the filter surface onto the blood vessels and may be able to reduce bleeding.

In addition, the micrographs indicated that the brains of animals receiving the transplants displayed distinct changes in glial reaction around the transplant when compared with those of the same age receiving untreated implants. Implantation of naked filters into P14 or older animals consistently resulted in rampant tissue degeneration, followed by the formation of a dense, flat-cell form of glial scar associated with extensive basal laminae and collagen fibers (see FIG. 10).

In contrast, the majority of animals given transplants of activated immature glia (i.e. postnatal day 2 through 8) showed no scar formation, little basal lamina production, and negligible amounts of tissue necrosis and bleeding. In essence, the host gliotic response in transplanted animals became indistinguishable from animals implanted with naked implants during critical stages (FIGS. 10c, 10d). The transplanted animals also showed an anti-laminin staining pattern identical to that seen in mice implanted on P2 (compare FIGS. 6a and 6b with FIGS. 6e and 6f). Most transplants examined 3-6 days after insertion showed (in regions where donor glia were present) little or no cellular debris and only a few macrophages at the donor/host interface (See FIGS. 10c, 10d, 11). The astrocytes along the surface of the implant formed multiple branches that interdigitated with the injured cortex, appearing to "knit" the artificial material with the tissue of the living host. In such animals (lateral to the longitudinal fissure), normal-appearing neuropil was present as close as one cell layer from the transplant (FIG. 11). In these successfully transplanted animals, there was minimal invasion of arachnoidal cells into the wound site. However, in a few instances, dense collagenous scars with layers of basal lamina, fibroblasts, and flattened glia were located in discrete regions of tissue adjacent to areas of the transplant. This occurred primarily in those regions that lacked the penetrating, stellate form of astrocyte.

6.2.7. Induced Axon Growth Over Glial Transplants

In the coronal sections of a number of the postcritical period animals which had received implants with transferred glia, several hundred "regenerating" or sprouting axons were observed at the previously lesioned cerebral midline among the transplanted glia attached to the implant (see FIG. 12). The axons were all unmyelinated (as expected for a newly regenerated axon) and bundled in small fascicles surrounded by glia.

6.3. Discussion

A summary of the results produced in the above example is set forth below in Table I.

TABLE I

Changes that Occur During and After Gliotic Reaction Induced When Acallosal Mice Are Implanted With Nitrocellulose Filters at Critical and Post-Critical Stages, and When Implants Are Transplanted From Neonates to Post-Critical-Period Animals[1]

|  | Critical | | Post-critical | Transplant |
|---|---|---|---|---|
|  | P2 | P8 | P14-adult[2] | P2 to P17,34[3] |
| Number of inserted GFAP+ cells | +++ | ++ | − | ++ |
| Laminin along glial processes in filter | + | + | − | + |
| Axon outgrowth over filter | +++ | ++ | − | + |
| Necrosis | − | + | +++ | + |
| Blood surrounding filter | − | + | +++ | + |
| Basal lamina | − | + | +++ | + |
| Collagen | − | + | +++ | + |
| Astrocyte shape | Stellate | | Flat | Stellate |
| Inserted glial processes | +++ | ++ | − | ++ |
| Time for glial to react to implant | 24–48 hours | | 5–7 days | |

[1]The +− system represents an overall impression of the observable presence or absence of the described reactions.
[2]Untreated implants.
[3]Implants from P2 critical period mice.

The present example demonstrates the existence of a "critical period" of less than postnatal day 8 for substrate-support axon regeneration. The de-novo growth of commissural axons across the cerebral midline was observed in acallosal animals implanted with untreated Millipore on or prior to postnatal day 8. In addition, the retrograde labeling studies using horseradish peroxidase showed that such fibers originated from cells of the cortex and terminated in the appropriate homotopic locations in the opposite hemisphere of the brain.

Moreover, in young mice (implanted before day 8) astrocytes did not produce a scar around a filter but instead sent many processes into the pores of the filter where the immature astrocytes produced a substrate which supported blood vessels and neurite growth. However, the results indicated that astrocytes in older mice (implanted on or later than postnatal day 14) failed to incorporate the filter within the brain and, instead, produced a glial-mesenchymal scar which did not support axon growth. The change in the brain's response to wounding, incorporation of implant, and support of axon growth indicated the presence of a "critical period", for substrate supported axon-elongation.

During the critical period, the migration of astrocytic glia onto the implant and the insertion of their processes are extremely rapid events occurring within 12–24 hours. The activated astrocytes were stellate-shaped and supported axonal elongation. During and after the initial glia invasion phase, the population of cells that moved onto the implant had the capacity to support the growth of axons, as well as vascular elements. The majority of these cells were GFAP+ astrocytes and, while in their youth, they not only have the ability to erect a three-dimensional network of processes separated by wide extracellular spaces, they also appear to respond to the presence of growing axons by extending additional cytoplasmic processes around the fibers.

In contrast, the results from the above example indicated that the reactive glial response in animals implanted 14 days or later after birth showed distinct differences from gliosis observed in neonates. The length of time it took glial cells to reach the surface of the implant site, the extent of secondary necrosis, the degree of basal lamina production and fibroblast contamination, and the density of tissue at and around the implant all increased with age (see Table I). The morphology of cells surrounding the implant also became altered (i.e. became flat as opposed to stellate in shape) and, most importantly, these cells lost their ability to stimulate axon outgrowth. Thus, in contrast to adult "reactive" gliosis (i.e. greater than postnatal day 14), the gliotic response in neonatal mammals (i.e. on or prior to postnatal day 8 in mice) is an active rather than reactive phenomenon and, when controlled geometrically with a prosthesis, can be considered a beneficial and constructive process.

As a result of the above discovery, activated immature astrocytes were transplanted into older animals to determine whether their "activated" effect could be transferred into the older animals to reduce the amount os tissue degeneration and glial scarring, as well as to determine whether the activated immature astrocytes could reestablish an environment conductive to axon regeneration. The results of the $^3$H-thymidine tests indicated that when activated astrocytes were removed from a neonate (retaining structural integrity with a polymer prosthesis) and transferred to a more mature or adult acallosal animal, that most of the activated astrocytes were indistinguishable from "critical" stage mice implanted with naked implants. Hence, the above results indicate that when activated immature astrocytes were implanted into an adult acallosal animal, an environment conducive for axon regeneration was reestablished in the host animal.

Moreover, the micrographs indicated that there was no evidence of tissue necrosis or persistent bleeding or scarring in the transplanted animal. The lack of extensive tissue degeneration and bleeding and scarring in the transplanted animals suggests that the transplanted astrocytes increased the survivability of cortical tissue near the site of the injury. Thus, the results demonstrate that the transplantation of "activated" immature astrocytes into post-critical period animals buffers the traumatic effect of the wound itself.

7. EXAMPLE: TRANSPLANTATION OF PURIFIED ACTIVATED IMMATURE ASTROCYTES INTO POSTCRITICAL PERIOD ANIMALS

7.1. Materials and Methods

7.1.1. Preparation of Purified Activated Immature Astrocytes

A highly purified population of "activated" murine immature astrocytes (before postnatal day 8 astrocytes) was prepared according to the following process. Cerebral cortices of four newborn C57 BL/6J mice obtained from the Jackson Laboratories were collected and cut into 1 mm pieces in 5 ml of calcium, magnesium-free Minimal Essential Medium (MEM-CMF). Trypsin (50% volume at 0.10%) was then added and the cells were incubated for 30 minutes at 37° C. Ethylenediamine-tetraacetic acid (EDTA) was then added (1 ml of 0.025% EDTA/5 ml of MEM-CMF) and incubated for 10 minutes. After incubation, the supernatant was then carefully removed and replaced with 2-3 ml of a mixture containing soybean trypsin inhibitor (SBTI, 0.52 mg/ml), deoxyribonuclease (0.04 mg/ml) and bovine serum albumin (3 mg/ml) in Dulbecco's Modified Eagles Medium (DMEM). The tissue chunks were gently mixed and allowed to settle. The supernatant was removed and replaced by DMEM with 10% fetal calf serum (FCS). The tissue was triturated 5 times through a fire polished pasteur pipette. This was repeated once more with a second pipette that was fire polished a little longer so that the opening was approximately one third the diameter of the original pipette. The cell suspension was placed on ice (in a sealed 15 ml conical centrifuge tube) for 5 minutes and then centrifuged for approximately one minute at 100 rpm. The cell supernatant containing a suspension of single cells was transferred to another tube.

The cells were then counted and plated at a density of 2.0 to $10^7$ cells/25 cm in a flask which had been previously coated with 0.1 mg/ml polylysine. The cells were pelleted by centrifugation at $1000 \times g$ and suspended in 5 ml of 50% astrocyte conditioned medium (i.e., medium that had been taken from another 4 day culture containing astrocytes only) in DMEM containing 10% FCS. The majority of the astrocytes usually attached themselves to the culture plate within six to eight hours. Within this period of time, few neurons and non-astrocyte cells were attached to the dish. The non-astrocyte cells could easily be removed when the flask was shaken vigorously by hand. The cell suspension was then removed and fresh medium was added.

The cycle of shaking was repeated several times until only a few rounded cells appeared among the spreading cells. The cultures were shaken and refed once a day until all of the rounded cells were removed. This usually took three days. Hence, the resulting activated immature astrocytes obtained by this process were usually postnatal day 4 in development.

In order to obtain activated immature astrocytes which are embryonic, as opposed to postnatal in development, the above procedure was repeated utilizing embryonic day 18 (E18) fetal rat donors.

7.1.2. Preparation of Mature (P14 or Older) Astrocytes

A portion of the above immature astrocytes were allowed to develop into mature astrocytes by the following procedure. Within 5-7 days after the initial plating, the astrocytes cultures became confluent. To replate the astrocytes, the media was removed, the cells were washed with MEM-CMF containing 0.02% EDTA and trypsin. This mixture was removed and only a few drops of this fresh medium was added back. The astrocytes were then incubated for 5-10 minutes until cells detached from the plates, suspended in DMEM and 10% FCS and transferred to a 76 cm culture flask. Two days after replating, the cultures were treated with a 2 day pulse of cytosine arabinoside (Ara-C) ($2.5 \times 10^{-5}$ M). The addition of Ara-C after each replating left a few dead cells, but controlled the proliferation of fibroblasts. Mature astrocytes were harvested from cultures 28 days or older.

7.1.3. Seeding of the Nitrocellulose Implants

The astrocytes produced above were removed from their cultures using MEM-CMF containing 0.02% EDTA and trypsin. After approximately 10 minutes, cold DMEM with SBTI and deoxyribonuclease (DNase) were added to the cell suspension. The cell suspension was then pelleted by centrifugation at 1000 g for five minutes. The supernatant was removed and the astrocytes were resuspended in 1 ml DMEM. The astrocytes were then pelleted and resuspended in DMEM a total of three times, the last in only 200 $\mu$l Cell viability and number were then determined by using trypan blue exclusion, which showed that many cells survive the procedure.

The implants to be inserted into the forebrains and spinal cords of the host animals were prepared out of various pore sizes of nitrocellulose filter paper. The implants to be inserted into the forebrain of postnatal day 60 (P60) acallosal mice were prepared out of 0.45 $\mu$m pore size nitrocellulose filter paper and were of the same "home plate" shape and size as the implants defined in Example 1 (i.e. 1-mm$^2$). The implants to be inserted into the dorsal root entry zone (DREZ) of the spinal cords of the root-lesioned adult rats were prepared out of 8.0 $\mu$m pore size nitrocellulose filter paper and were "pennant" shaped and of a size approximately 0.75-1.0 mm $\times$ 3.0 mm $\times$ 250 $\mu$m. See FIG. 18.

Approximately 10 ml of the activated immature astrocytes were then seeded onto the nitrocellulose implants at a density of $10^7$ cells/ml (about $10^5$ astrocytes/implant). The astrocytes suspension usually formed a bead on the surface of the filter, and was incubated for two hours at 37° C. A 100 $\mu$l drop of DMEM was then carefully placed over the nitrocellulose implant and the astrocytes were allowed to attach themselves to the filter by incubation overnight.

The above seeding process was then repeated to produce the comparison implants containing the mature mouse astrocytes. However, mature (P14 or older) mouse astrocytes were substituted for the activated immature astrocytes.

7.1.4. Implantation of the Glial-Coated Filters

7.1.4.1. In the Forebrain of the Postnatal Day 60 Acallosal Mice

The forebrain "home plate" shaped implants coated with the activated immature astrocytes were inserted into eight postnatal day 60 acallosal mice according to the procedure set forth in Example 1. For comparison purposes, "home plate" shaped implants coated with mature (P14 or older) implants were also implanted in a similar number of postnatal day 60 acallosal mice by the same procedure utilized above.

7.1.4.2. In the Dorsal Root Entry Zone of the Spinal Cord of the Postnatal Day 180 or Older Rats Postnatal day 180 or older (200-250 gram) rats obtained from Charles River Facilities were anesthetized. A laminectomy was performed over dorsal roots L4-L6 to expose them and their entrance points into the cord. Dorsal roots L4 and L6 were cut as a means of control to localize the sensory perception of dorsal root L5. Dorsal root L5 was subsequently crushed (3× for 10 seconds). Dorsal root L5 was then traced to the dorsal root entry zone in the spinal cord where a 1.5-2 mm superficial incision (approximately 0.5 or less mm in depth) was made into the spinal cord between the dorsal root (L5) and posterior columns. The pennant shaped implant coated with activated immature rat astrocytes was then inserted superficially into the incision. See FIG. 18. The pole portion of the pennant-shaped implant was pushed gently into the root. Thus, while the broad portion of the pennant laid in the cord proper, just medial to the dorsal horn, the pole portion of the pennant-shaped implant protruded gradually outside the spinal cord and into the dorsal root itself.

The incision and pennant were then covered with sterile gelfilm and the muscles and skin were sutured to cover the wound. At 2 day intervals for three weeks to one month the rats were tested to see if they had recovered any of their L5 dorsal root sensory motor behavior. In addition, after 21-30 days, the rats were sacrificed and serial sections of the implant and surrounding tissue region were prepared for examination according to the procedure set forth in Example 1.

7.1.5. Immunohistochemistry and $^3$H-Thymidine Autoradiography of the Transplants The same procedures set forth in Example 1 were applied to the immature and mature astrocytes of the present examples.

7 2 Results

7.2.1. Transplantation of Purified Astrocytes into the Forebrain

The transplantation of activated immature purified astrocytes into the forebrain of postnatal day 60 (P60) mice repressed scar formation in five out of the eight mice tested. These transplanted animals resembled those receiving non-glial coated implants on postnatal day 8 (P8). Scar formation was repressed over the majority of the implant surface. In addition, the immunocytochemical staining of immature astrocytes transplanted into postnatal day 60 (P60) mice indicated that the cells attached to the implants were GFAP-positive and many had processes deep within the pores of the filter. The $^3$H-thymidine autoradiography results of the transplants showed that after seven days following astrocyte insertion into the brain, labeled cells often were found away from the implant surface (see FIG. 13).

To determine the amount of scar surrounding the transplants, sections consecutive to that in FIG. 13a were stained with antibodies against laminin protein. On the dorsal portion of the implant, which was the side coated with astrocytes from culture, the laminin staining pattern was confined to the filter surrounding astrocyte processes and to the basal lamina surrounding blood vessels (see FIG. 13c). This staining pattern was similar to that observed with neonatal-implants and the transplants of Example 1. At the bottom (ventral part) of the filter, basal lamina within the scar was apparent. This area did not show GFAP-positive astrocyte processes within the implant. Since astrocytes were only plated on the top portion of the filter, scar formation at the bottom of the filter was a consistent feature of all transplanted adults receiving implants. The uncoated bottom portion of the filter also served as an internal control.

When astrocytes were allowed to mature in culture for 28 days, their relative size greatly increased and their rate of division decreased. Shortly after replating, mature astrocytes hypertrophy, in which the astrocytes spread to sizes between 50 to 120 μm.

In contrast to the immature astrocyte transplants, transplantation of mature astrocytes on filters (28 days or more in culture) failed to repress scar formation (see FIG. 14). In such animals, thick dense scars covered the majority of the implant surface (see Table II below and FIG. 14). Electron micrographs of the transplant showed that the scar was similar in morphology to that which occurred when untreated filters were implanted into adult forebrains. The scar was predominantly composed of fibroblasts and astrocytes. Extracellular matrix components such as basal lamina and collagen were also present (FIG. 15b). Importantly, mature astrocytes labeled with $^3$H-thymidine prior to transplantation did not migrate out of the scar and many remained attached to the implant (see FIG. 13f). This was remarkably different from transplants of immature astrocytes (compare FIG. 13c to FIG. 13f).

TABLE II

| | | Area of Implantation | |
|---|---|---|---|
| Age | | Scar Formation | Glial Incorporation |
| P2-48 hr | n = 20 | 2.15 +/− 0.78 | 38.6 +/− 9.07 |
| P8-48 hr | n = 10 | 8.2 +/− 2.71 | 30.6 +/− 9.75 |
| P14-7 days | n = 6 | 26.8 +/− 11.07 | 17.0 +/− 7.02 |
| P21-7 days | n = 16 | 35.75 +/− 9.02 | 5.3 +/− 1.70 |
| Trans P2 to P34 | n = 15 | 5.4 +/− 1.81 | 35.5 +/− 8.94 |
| In vitro 2 days to P60 | n = 8 | 12.5 +/− 1.19 | 38.0 +/− 0.75 |
| In vitro 28 days to P60 | n = 10 | 43.6 +/− 4.9 | 5.2 +/− 5.0 |

This table quantitatively illustrates the amount of scar which forms on the surface of the implant at different ages or conditions. Scar formation was quantified by dividing the dorsal portion of the filter surface into numerous grids (each approximately 50 μm). Each grid was scored and counted for scar formation or the ability of the glia to incorporate the implant into the host brain according to definitions described above. The amount of scar formed after implantation into P2, 8, or P34 transplants is greatly reduced when compared to animals implanted on P14 or older. Difference between acallosal mice implanted on P21 and those implanted on P2, 8, or transplanted is significant to P less than 0.01.

7.2.2. Transplantation of Purified Activated Immature Astrocytes into the Dorsal Root of the Spinal Cord The micrographs obtained of the pennant-shaped nitrocellulose implant coated with purified activated immature rat astrocytes inserted in the dorsal root of the spinal cord indicate that the combination of embryonic represses scar formation locally in the spinal cord dorsal root entry zone (DREZ) and stimulates axons and blood vessels to enter the central nervous system along the implant surface. (See FIGS. 19a through 19c). In addition, the horseradish peroxidase (HRP) labelling studies of the previously lesioned L5 root show many fibers and terminals with buttons in their proper positions of laminal 2 and 3 within the dorsal horn. The exact relationship of the incoming fibers with the implant surface and the presence of a number of novel terminal arbor malformations in a subpopulation of the axons provides convincing evidence that the fibers in the cord are truly regenerated.

Moreover, six (6) of the nineteen (19) rats implanted with the pennant-shaped nitrocellulose implants coated with activated immature rat astrocytes exhibited functional recovery of many of their basic sensory motor behaviors approximately 5 to 7 days following insertion of the implants. This functional recovery was shown to be due, at least in part, specifically to the promotion of nerve regeneration, as demonstrated by the loss of functional recovery upon relesion of the nerve growing along the nitrocellulose implant. Hence, the above results demonstrate that activated immature astrocytes seeded onto nitrocellulose implants promote directed axonal and blood vessel regeneration and repress glial scar formation in the spinal cord.

8. EXAMPLE 3: IMMORTALIZATION OF THE ACTIVATED IMMATURE ASTROCYTES

Purified activated immature (postnatal day 0) rat cortical astrocytes produced according to the process set forth in Example 2 were immortalized with defective retrovirus coding for SV40 T antigen and bacterial neomycin resistance genes by the following procedure. The purified activated immature astrocytes were seeded at about $5 \times 10^5$ cells per 60 mm dish on day 1. On day 2 the medium was replaced with 2 ml of the viral supernatant containing the defective retrovirus coding for SV40 T antigen and bacterial neomycin resistance genes (obtained from Dr. P. S. Jat, University College at London, London, England). The cells were incubated for 2-3 hours and then the virus was removed and fresh medium was resupplied. Neomycin resistant colonies were selected with medium containing G418 (a neomycin analog obtained from Gibco, Grand Island, N.Y.). Colonies which displayed astrocyte morphology were selected and cultured over a period of months, and were passaged without undergoing microscopically observable change. The clones were then stained for glial fibrillary protein and tested for promotion of axonal growth. The clones were GFAP-positive and promoted axonal growth to a similar extent as immature primary rat astrocytes, and thus the activated immature phenotype was preserved.

9. EXAMPLE: ASTROCYTES MATURATION REDUCES NEURITE OUTGROWTH AND NEURONAL ADHESION IN VITRO

We have examined neurite outgrowth on, and neuronal cell adhesion to, purified populations of immature and mature astrocytes in vitro. We show that the rate of neurite outgrowth is consistently reduced over the surface of mature astrocytes compared with immature astrocytes, and in short term adhesion assays, neuronal cell body adhesion is dramatically reduced on mature compared to immature astrocytes. These effects appear to be mediated through cell-surface changes in the astrocytes.

9.1. Materials and Methods

9.1.1. Preparation of Purified Astrocytes

Purified astrocytes were prepared from new born rat cerebral cortices using a modification of the method described by Cohen (1983, Handbook of Laboratory Methods, University College, London). Briefly, cerebral cortices were carefully dissected from newborn mice, the meningeal tissue stripped off, and cells dissociated by incubation in 0.025% trypsin in calcium-magnesium free buffer (MEM-CMF) for 30 minutes. Cells were pelleted at $1000 \times g$ for 5 minutes, resuspended in 5 ml of 50% astrocyte conditioned medium in DMEM containing 10% FCS and plated in polylysine coated (0.1 mg/ml) 75 cm$^2$ tissue culture flasks at a density of $2.01 \times 10^7$ cells/flask and incubated at 37° C. with 5% $CO^2$ for 4-6 hours. Non-adherant cells were removed by shaking and the media was changed. Greater than 95% of the cells that remain attached to the flask following this procedure were astrocytes as defined by staining with antibodies to GFAP, and although these cells assumed various morphologies, greater than 95% had an antigenic phenotype similar to type-1 optic nerve astrocytes (Raff, M. C., et al., 1983, J. Neurosci. 3:1289-1300). Immature astrocytes were harvested after two further days in culture, while mature astrocytes were harvested after a further 28 days in culture. Cells were removed from tissue culture flasks by incubation in 0.025% EDTA and 0.025% trypsin in MEM-CMF for 15 minutes. They were pelleted at $1000 \times g$ for 5 minutes, resuspended in DMEM-F12, 10% FCS to such a concentration that 25 μl of medium contained 60,000 astrocytes, and plated onto a central region of polylysine coated glass coverslips to form confluent monolayers.

9.1.2. Preparation of Cortical Neurons

Highly enriched populations of embryonic cerebral cortical neurons were prepared from embryonic day 18 (E18) rats. The cerebral cortices were dissected, meninges removed, and the tissue cut into approximately 1 mm$^3$ pieces. Tissue was incubated in calcium-magnesium free buffer (CMF) containing 0.01% trypsin and 0.025% EDTA for 30 minutes, an equal volume of DMEM containing 10% FCS and 0.05 mg/ml DNase was added and the incubation continued for a further 5 minutes. Cells were dissociated by trituration, pelleted at $1000 \times g$ and resuspended in DMEM-F12 with 10% FCS. Debris and non-dissociated cells were removed by passage through a 30 μm nylon filter and the resultant cell population plated at a density of approximately $2.5 \times 10^6$ cells/25 cm$^2$ poly-l-lysine coated flask and incubated for 4 hours at 37° C. in 5% $CO_2$. The media was then replaced with 3 ml of 0.025% EDTA in MEM-CMF (Spinners) and incubated for a further 20 minutes. Neurons were detached from the substrate by gentle shaking and removed from the flask with the medium. After chilling on ice, cells were pelleted and resuspended in DMEM-F12 containing 1.0% FCS and 2 mM sodium pyruvate.

9.1.3. Quantitation of Neurite Outgrowth

To quantify neurite outgrowth, 1 ml of media containing 5000 neurons form E18 cerebral cortices was plated onto the surface of an astrocyte monolayer or a non-cellular substrate (laminin, astrocyte conditioned media etc.). The extent of outgrowth was assayed 16, 28 and 40 hours after plating as described below.

Neurons were identified by labelling with the C fragment of tetanus toxin conjugated to texas red (a gift from Dr. N. Robbins). Cultures were incubated for 30 minutes at room temperature in a 1:20 dilution of the tetanus toxin conjugate in phosphate buffer in the presence of 50% normal goat serum (NGS) or 5% BSA. After washing, cultures were fixed with 4% paraformaldehyde and mounted in 5% n-propyl gallate in glycerol. For double labelling experiments, following fixation, cultures were permeablized with acid-alcohol at −20° C. and incubated in anti-GFAP serum (Pruss, R. M., 1979, Nature 280:688–690) at a dilution of 1:1000 in PBS and 10% NGS for 1 hour at room temperature, washed, and incubated in goat anti-rabbit Ig conjugated to fluorescein (G RIg-FITC) (Capel) at a dilution of 1:100 in PBS and 10% NGS for 1 hour at room temperature. Cultures were washed, mounted and examined with a Nikon optiphot photomicroscope equipped with epifluorescence.

Individual neurites grown for 28 hours on substrates of either poly-l-lysine (100 μg/ml), laminin (25 μg/ml), immature or mature astrocyte conditioned media, and a combination of laminin and astrocyte conditioned media were also photographed for measurement. Astrocyte conditioned media was obtained by incubating confluent monolayers of astrocytes in DMEM-F12 without serum for 48 hours prior to addition to coverslips. Polylysine coated coverslips were treated with laminin and/or astrocyte conditioned media for 8 hours or overnight prior to the addition of neurons. Neurons grown on astrocyte conditioned media treated coverslips were also plated in the presence of 50% astrocyte conditioned media.

Photomicrographs of individual neurons with clearly identifiable neurites were taken using a 20× fluoro/phase lens on tri-X film rated at 400 ASA. The 35 mm negatives were projected at a fixed magnification onto the screen of a Vanguard Motion Analyzer and lengths of individual neurites measured using a Numonics digitizer. For each time point, 30–40 neurites were measured over both immature and mature astrocytes in three separate experiments. The data was pooled and the mean of the longest neurites was calculated. Comparison of neurite lengths was made using standard student T-test.

9.1.4. Short Term Neuronal Adhesion Assay

To compare the adhesive properties of immature and mature monolayers of astrocytes for cortical neurons, E18 cortical neurons were labelled with fluorescein diacetate (Rutishauser, U., et al., 1976, Proc. Natl. Acad. Sci. U.S.A. 73:577–581). Neurons dissociated from E18 rat cerebral cortices were incubated in 200 μg of fluorescein diacetate in 10 ml DMEM at room temperature for 15 minutes. Labelled cells were then pelleted at 1000×g for 5 minutes, washed, and resuspended to a concentration of $5 \times 10^5$ neurons/ml in DMEM. One ml of cell suspension was added to an individual well in a 24 well plate containing a coverslip coated with a monolayer of either immature or mature astrocytes, incubated for 30 minutes on a rotating shaker at 75 RPM at room temperature and gently washed to remove non-adherent neurons. Neuronal adhesion was assayed by counting the number of attached labelled neurons in 30 consecutive randomly selected fields under fluorescein optics using a 20× lens.

9.1.5. Electron Microscopy

Cultures of young and old astrocytes, removed at the time of plating neurons, were fixed by immersion in a fixative containing 3% paraformaldehyde, 1% glutaraldehyde in 0.12 M phosphate buffer. Cells were fixed for 3 hours at room temperature, washed in buffer and post fixed in 1% osmium tetroxide for 1 hour on ice. After washing, cultures were en-block stained with 0.5% aqueous uranyl acetate for at least 4 hours at 4° C., washed, dehydrated through graded alcohols and embedded in Epon 812 resin. After removal of the glass coverslip, en-face sections were cut on an LKB microtome, stained with uranyl acetate and lead citrate and examined on a JEOL 100 CX electron microscope at 80 KV.

9.2. Results

9.2.1. Neuronal Morphology on Immature and Mature Astrocytes

Figure 20A:
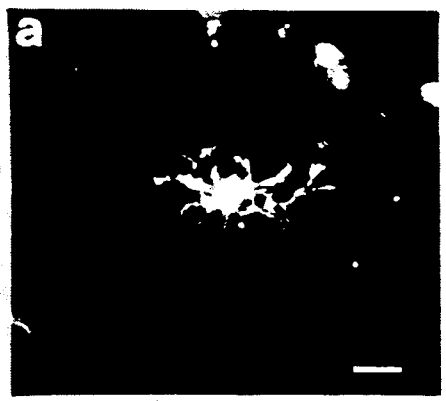
Figure 20B:
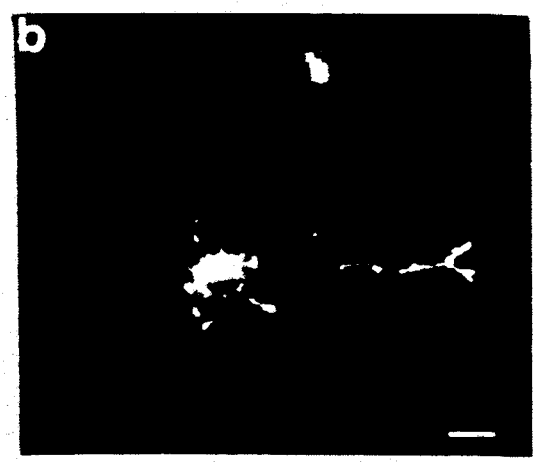
Figure 20C:
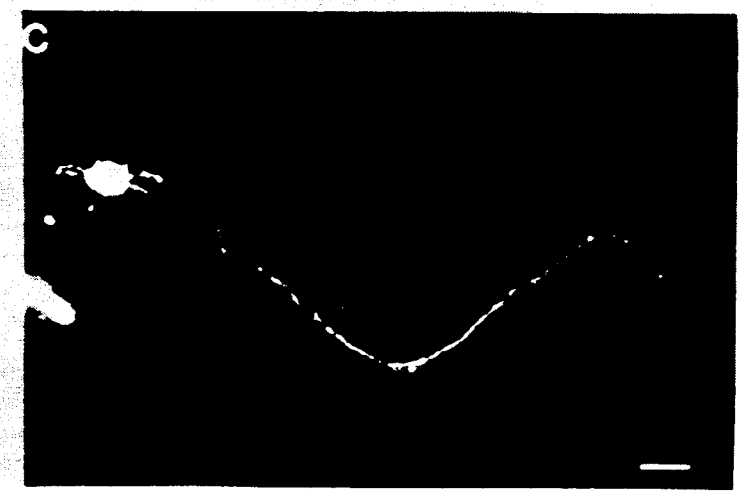
Figure 21A:
Figure 21B:
Figure 21C:
Figure 21D:
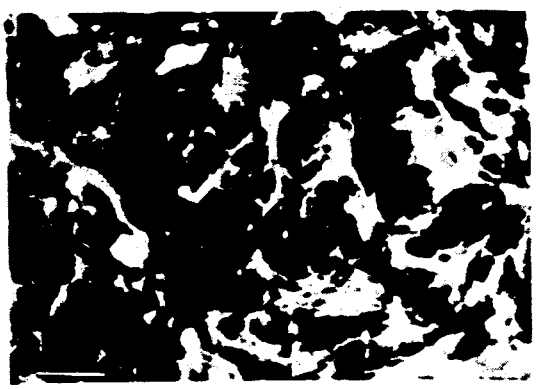
Figure 21E:
Figure 21F:
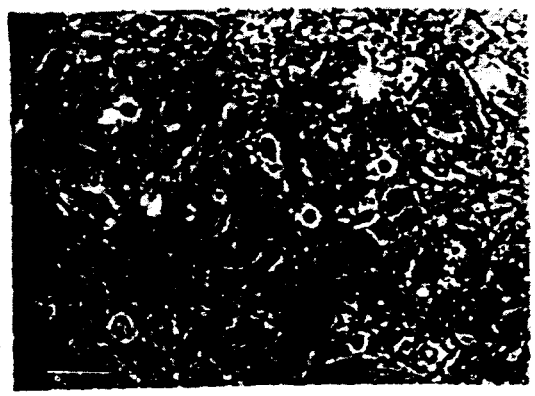

Embryonic neurons grown on immature and mature astrocytes assumed a variety of different morphologies. They could be broadly categorized into three distinct classes. Approximately 30% of the neurons extended multiple neurites of similar length and lacked any long axon-like projection (FIG. 20A). Neurons with this morphology may represent interneurons in the intact CNS. Approximately 40% of the neurons extended many short neurites and a single long neurite 2–3 times the length of the other neurites (FIG. 20B). Neurons with this morphology may represent short projection neurons in the intact CNS. Approximately 25% of the neurons extended many short neurites and a single very long neurite often with an identifiable growth cone (FIG. 20C) and may represent long projection neurons in the intact CNS.

To determine if these different cell morphologies represented distinct populations of neurons, or a maturation of cells extending multiple short neurites to those which form long projection neurites, we examined the number and morphologies of the neurons that attached to young and old astrocyte monolayers at different times after plating. We found that the relative numbers in each class of neurons were similar on both young and old astrocytes (Table III), and in both cases the number of neurons that survived and sent out processes was very similar (Table III).

TABLE III

| RELATIVE NUMBER OF EACH TYPE OF NEURON ON IMMATURE AND MATURE ASTROCYTES AFTER 28 HOURS* | | |
|---|---|---|
| Neuron type | Immature (P1–3d) Astrocytes | Mature (P1–34d) Astrocytes |
| Interneuron (a) | 34.25 +/− 3.11 | 34.25 +/− 2.56 |
| Short Projection (b) | 38.00 +/− 2.93 | 38.12 +/− 2.36 |
| Long Projection (c) | 23.75 +/− 4.11 | 23.12 +/− 1.13 |
| Total | 96.00 +/− 9.26 | 95.50 +/− 5.00 |

*Neurons plated on the surface of astrocyte monolayers were cultured for 28 hours, labelled with tetanus toxin and examined as described in methods. Twelve randomly selected fields were classified on their morphology as shown in FIG. 20. Note that the survival of the different populations of neurons is very similar on both immature and mature astocytes.

Although with longer culture periods the length of the longest neurites increased, the ratio of the number of neurons with different morphologies was nearly identical at 16, 28 and 40 hours after plating. These observations suggest that the three classes of morphologically distinct neurons seen in these cultures represent distinct populations of CNS neurons, and that the number and relative proportions of neurons that survived was similar on both young and old astrocytes.

9.2.2. Differences in Neurite Outgrowth over Immature and Mature Astrocytes

Comparison of neurite outgrowth over the surface of young and old astrocyte monolayers 16 hours after plating showed that neurites growing over the surface of immature astrocytes appeared longer than the neurites from a matched population of cells growing over the surface of mature astrocytes (FIG. 21; compare a and b). This difference was also apparent when neurons were grown for 28 or 40 hours over either immature or mature astrocytes. To determine more precisely the difference in neurite length on the two glial substrates, the length of the longest neurites were measured for 100 neurons at each time point.

At all three time points, neurons growing on the surface of the young astrocytes extended neurites that were approximately 30% longer than those neurites extending from neurons growing on the surface of old astrocytes (Table IV).

TABLE IV

| NEURITE OUTGROWTH OVER IMMATURE AND MATURE ASTROCYTES* | | | | |
|---|---|---|---|---|
| Astrocyte Type | Outgrowth Time (hours) | Length of Neurite Outgrowth (μ) | | |
| | | Longest | +Branches | Total |
| Immature | 16 | 215.1 +/− 26 | 252.1 +/− 33 | 316.5 +/− 63 |
| | 28 | 372.6 +/− 38 | 421.9 +/− 48 | 527.5 +/− 78 |
| | 40 | 490.5 +/− 53 | 549.4 +/− 60 | 702.8 +/− 102 |
| Mature | 16 | 141.1 +/− 17 | 167.1 +/− 22 | 231.5 +/− 46 |
| | 28 | 263.0 +/− 26 | 298.7 +/− 32 | 390.5 +/− 56 |
| | 40 | 341.1 +/− 37 | 394.6 +/− 42 | 556.2 +/− 82 |

The rate of neurite extension over the glial surfaces appeared relatively linear over the time course of the experiment (FIG. 22), although it was always more rapid over the surface of young astrocytes than over the surface of old astrocytes.

To determine if this apparent more rapid rate of neurite extension on the surface of the young astrocytes reflected a decrease in neurite branching, the total length of the longest neurite and its associated branching was measured. Again, a 30% increase in outgrowth was found on the surface of young astrocyte monolayers compared to old astrocyte monolayers (Table IV). To ensure that this increase in the length of the longest neurite represented an increase in neurite production and not a redistribution of neurite extension, the total neurite outgrowth from neurons on the surface of immature and mature astrocyte monolayers was compared. Total neurite outgrowth was more than 25% greater from neurons on the surface of immature astrocytes than it was from neurons on the surface of mature astrocytes, suggesting that those neurons associated with immature astrocytes synthesized comparatively more neurites than those neurons on the surface of mature astrocytes.

9.2.3. Neurite Outgrowth in the Presence of Conditioned Medium From Immature and Mature Astrocytes To determine if the difference in neurite outgrowth over the surface of immature and mature astrocytes resulted from the release of different soluble factors by the astrocyte monolayers or was mediated directly through interactions with the astrocyte surface, neurite outgrowth was examined in the presence of immature and mature astrocyte conditioned media. Comparison of neurite outgrowth over a poly-l-lysine substrate alone, or poly-l-lysine treated with either immature, mature astrocyte conditioned media, or a combination of laminin and either immature or mature astrocyte conditioned medium indicated that both young and old astrocyte conditioned media resulted in a similar increase in axonal growth over that seen on a polylysine substrate. The extent of this neurite outgrowth was comparable to that seen over the surface of laminin coated polylysine. The addition of astrocyte conditioned media to laminin coated coverslips did not result in any additional increase in axonal outgrowth (Table V).

TABLE V

| NEURITE OUTGROWTH ON NON-CELLULAR SUBSTRATES* | | |
|---|---|---|
| Substrate | | Length of Longest Neurite (μm) |
| Poly-l-lysine | n = 57 | 54.4 +/− 21.2 |
| Laminin | n = 51 | 153.2 +/− 26.9 |
| Immature Astrocyte Condition Media | n = 51 | 144.7 +/− 30.5 |
| Mature Astrocyte Condition Media | n = 54 | 138.0 +/− 32.8 |
| Laminin + Immature Astrocyte Condition Media | n = 52 | 159.6 +/− 34.3 |
| Laminin + Mature Astrocyte Condition Media | n = 51 | 152.0 +/− 34.1 |

*Neurons plated on non-cellular substrates were measured after 28 hours in culture as described in methods. All coverslips were coated with 100 μg/ml polylysine. Laminin substrates were produced by coating with 50 μl of a laminin (25 μg/ml) for 8 hours. Media (DMEM-F12) was conditioned by confluent immature and mature astrocyte cultures for 48 hours prior to adding 50 μl to either poly-lysine or laminin coated coverslips. Note that laminin and conditioned media from both im mature and mature astrocytes result in a similar increase in neurite outgrowth over a polylysine substrate, but these increases do not appear to be additive.

In all cases, neurite outgrowth was >40% less on laminin and astrocyte conditioned media than over the surface of mature astrocyte monolayers (compare Tables IV and V). However, significant differences in neuronal morphology were seen on these substrates. On laminin, the majority of neurons extended few neurites, usually having only a single unbranched process, while in the presence of both young and old astrocyte conditioned media, although there appeared to be an increase in the number of neurites, this was always less than that observed from neurons grown on astrocyte monolayers.

9.2.4. Neuron Adhesion to Immature and Mature Astrocytes

To compare the adhesion of cortical neurons to monolayers of either immature or mature astrocytes, the relative number of attached neurons was determined following a short term adhesion assay. Neurons preferentially attached to the astrocyte monolayers, rather than the surrounding poly-l-lysine coated coverslip. The extent of neuronal adhesion to the surface of immature astrocytes was considerably greater than neuronal adhesion to the surface of mature astrocytes (FIG. 23). Quantitation of this adhesion showed an approximate 4 fold increase in the number of neurons binding to the surface of immature compared to mature astrocytes (Table VI).

TABLE VI

NEURON ADHESION TO ASTROCYTE MONOLAYERS*

| Astrocyte | Number of Neurons |
|---|---|
| Immature | 149 +/− 36 |
| Mature | 39 +/− 13 |

*Neurons at a density of $5 \times 10^5$ were plated on the surface of monolayers of immature and mature astrocytes for 30 minutes, and non-adherent cells were removed. Twelve random fields were counted from 3 different preparations as described in methods, and the data pooled. Note that there is a greater than three fold increase in the adhesion of neurons to immature astrocytes compared to mature astrocytes. Significance of difference using student T-test $P<0.001$.

9.2.5. Ultrastructural Characteristics of Immature and Mature Astrocytes

Figure 24A:
Figure 24B:
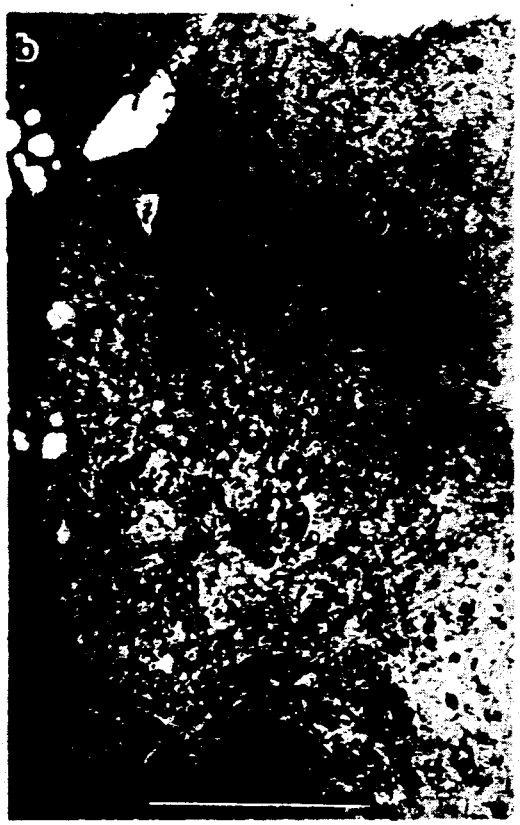
Figure 24C:
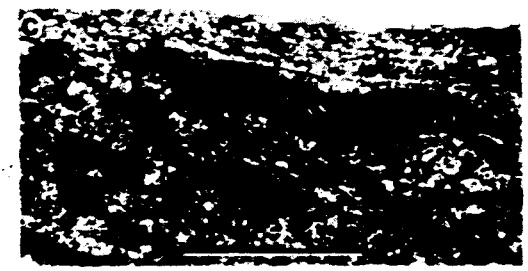
Figure 24D:

Maturation of forebrain astrocytes appears to cause a reduction in neurite outgrowth and neuron adhesion. This reduction may result from a reduction in viability or increase in cell death in the astrocyte cultures over time, or the replacement of the immature astrocyte phenotype by a mature astrocyte phenotype. To assess these possibilities, confluent monolayers of both immature and mature astrocytes were examined by transmission electron microscopy. Neither cultures exhibited signs of necrosis, or extensive cell damage, although the cells in both cultures expressed many characteristics of astrocytes in vivo (FIG. 24). However, morphological differences between the cells in the two cultures were evident. Immature astrocytes had a dense cytoplasm containing many closely packed organelles, few dense bodies and small numbers of intermediate filaments (FIG. 24a, b). The immature astrocytes were usually small, with few junctional specializations and large spaces between them filled with many thin cytoplasmic processes (FIG. 24a). By contrast, mature astrocytes had a less dense cytoplasm, containing less closely packed organelles, but many dense bodies and large numbers of intermediate filaments (FIG. 24c, d). The mature astrocytes were large cells and appeared to be in closer apposition with one another and contained many more junctional specializations between them (FIG. 24c). Thus, ultrastructurally it appears that the reduction in neurite outgrowth seen over the surface of mature astrocytes may reflect the development of a mature astrocyte phenotype and not a reduction in viability or increase in cell death of astrocytes during the culture period.

9.3. Discussion

We have previously shown that an enriched population of immature astrocytes transplanted into the forebrain of acallosal adult mammals have the capacity to suppress glial scar formation and support axonal growth, and that this capacity to support axonal growth appeared to be lost upon maturation of the astrocytes (see Sections 6 and 7, supra). Here we show that in vitro maturation of a purified population of astrocytes results in a reduction in both the capacity of these cells to support axon outgrowth and in their adhesive properties to neuronal cell bodies. These results provide direct evidence that maturation of astrocytes results in a reduction in their capacity to support neurite outgrowth and their adhesive properties for neurons.

From both morphological and functional analyses, the maturation of astrocytes appears to occur on a similar time schedule both in vivo and in vitro. These studies help identify what has been termed a "critical period" which ends around postnatal day 8 in rodents. This critical period was also apparent in cultured astrocytes, so that astrocytes removed from newborn mice brains and maintained in culture less than 7 days suppressed glial-scar formation and supported axonal growth when transplanted into an adult brain (Smith, G. M., and Silver, J., 1988, in Progress in Brain Research, Vol. 78, Ch. 45, Gash, O. M. and Sladek, J. R., Jr. (eds.), Elsevier Science Publishers). On the contrary, astrocytes removed from newborn brain and cultured for several weeks failed to support axon growth when transplanted into the adult brain (Smith, G. M., and Silver, J., 1988, in Progress in Brain Research, Vol. 78, Ch. 45, Gash, O. M. and Sladek, J. R., Jr. (eds.), Elsevier Science Publishers).

Given that astrocyte maturation in vivo and in vitro appears to result in similar morphological phenotypes, it was surprising that there was only a 30% reduction in the extent of neurite growth over the surface of mature compared to immature astrocytes in culture, since very limited axon growth is seen following a lesion to the adult CNS (Kiernan, J. A., 1979, Biol. Rev. 54:155-197). A number of factors may contribute to this apparent discrepancy. Recent studies have suggested that specific proteins found on the surface of oligodendrocytes and in myelin of the mammalian CNS but not PNS have the capacity to strongly inhibit axon outgrowth (Caroni, P., and Schwab, M. E., 1988, J. Cell Biol. 106:1281-1288; Schwab, M. E., and Caroni, P., 1988, J. Neurosci. 8:2381-2393). Given that myelin debris is generally present after lesions to the adult CNS, it would contribute to the inhibition of axon growth, while such myelin debris is absent from the purified astrocyte cultures. Furthermore, lesions to the adult CNS usually result in a gliotic response or gliosis. In vivo, gliosis consists of what has been termed "reactive" astrocytes which contain an abundance of intermediate filaments and intracellular junctions (Reier, P. J., et al., 1983, in Spinal Cord Reconstruction, Kao, C. C., et al. (eds.), Raven Press, N.Y., pp. 163-195; Nathaniel, E. J. H. and Nathaniel, D. R., 1981, in Advances in Cellular Neurobiology, Vol. 2, Academic Press, N.Y., pp. 249-301). Although mature cultured astrocytes also contain an abundance of intermediate filaments, intracellular junctions and have a large cytoplasmic volume, their relationship to "reactive" astrocytes in vivo is unclear. Thus, it is conceivable that a particular population of mature astrocytes in vivo may respond directly to a lesion and change in such a way as to totally inhibit axon growth. Another possible explanation for inhibition of axon regeneration by astrocytes at the DREZ has been proposed to result from either the formation of a physical barrier, or the activation of physiological stop mechanisms in the axons (Liuzzi, F. J., and Lasek, R. J., 1987, Science 237:642-645). If such a physiological stop mechanism is activated by astrocytes at the DREZ, why is it not activated by mature forebrain astrocytes in vitro? One possibility is that DREZ astrocytes but not forebrain astrocytes possess the capacity to inhibit axon outgrowth. While regional differences in CNS astrocytes have been observed (Chamak, B., et al., 1987, J. Neurosci 7(10):3163-3170), it seems more likely that the total inhibition of axon growth induced by the astrocytes of the DREZ may be the result of an architecturally different environment (Freed, W. M., et al., 1985, Science 227:1544-1552; Reier, P. J., 1986, in Astrocytes: Cell Biology and Pathology of Astrocytes, Fedoroff, S. and Vernadakis, A. (eds.), Academic Press, pp. 263-324). Thus, at the DREZ, growing axons are presented with a three dimensional matrix of astrocytes, while in culture growing axons are presented with only a two dimensional astrocyte substrate.

Although the molecular mechanism of inhibition of axon growth through a region of gliosis or at the dorsal root entry zone in the adult animals is unknown, one possibility is that it results from changes in the cell adhesion properties of the astrocytes. Considerable axon outgrowth may only occur when cell-cell adhesion was optimal. The finding that with maturation there appears to be a dramatic reduction in the adhesivity of astrocytes for neuronal cell bodies suggests that a decrease and not an increase in neuron/glial interactions is responsible for the reduction of axon growth through gliosis in the adult CNS.

A number of observations suggest that mature astrocytes do in fact represent a less adhesive substrate for growth cones than immature activated astrocytes. For instance, we have observed that neurons extending processes over non-confluent cultures of immature astrocytes invariably remained in association with the astrocyte surface rarely growing onto the poly-l-lysine coated coverslip, while neurons extending processes over non-confluent cultures of mature astrocytes frequently grew off the surface of the cells and onto the surrounding polylysine substrate. Such observations suggest that the surface of immature astrocytes represented a preferred substrate for axon growth compared to the surrounding surface, while immature astrocytes did not. Furthermore, when brain explants were plated on the surface of immature cultured astrocytes, neurite outgrowth appeared to be predominantly nonfasciculated. In contrast, when brain explants were plated onto the surface of mature cultured astrocytes, neurite outgrowth occurred in a predominantly fasciculated fashion. Since the degree of axon fasciculation has been suggested to reflect the relative adhesivity of a substrate (Rutishauser, U., 1984, Nature 310:594-587), such that a more adhesive substrate results in defasciculated neurite outgrowth while a less adhesive substrate results in fasciculated neurite outgrowth (Rahthjen, F. G., et al., 1987, J. Cell Biol. 104:343-353), these results also suggest that immature astrocytes represent a more adhesive substrate for the growing axon than do mature astrocytes.

In conclusion, we have shown that in vitro the ability of astrocytes to support CNS axonal elongation and bind CNS neurons is reduced as the astrocyte matures. We propose that this reduction in the capacity of mature astrocytes to support CNS neurite elongation, possibly through reduced adhesivity, may be an important component in limiting the extent of axonal regeneration in the adult mammalian CNS.

10. In Vitro Analyses of Astrocyte Cell Interactions at Different Ages

We have developed an in vitro model in which cells responding to trauma in the immature and mature CNS can be isolated, placed into serum-free culture and characterized. By implanting nitrocellulose filters into the brains of neonatal and adult rats under different conditions, we were able to harvest populations of cells responding to trauma in the neonate (critical period implant), in the adult (scar implant), and implants that have remained in vivo past the critical period (post-critical period implant). Upon placement in culture, we have found that astrocytes represent the majority of cells occupying both the critical period and post-critical period implants, whereas fibroblasts and macrophages represent the majority of cells in the glial-fibroblastic scar. The morphologies of the astrocytes on the surface of the different implants, after three days in culture, differs markedly—the critical period astrocytes exhibiting a more ordered distribution compared to the haphazard arrangement of astrocyte processes on the surface of the post-critical and scar implants. After migration from the implant, critical period astrocytes assume an epithelioid morphology and cluster together setting up definite boundaries betweeen themselves and the endothelial cells. In contrast, post-critical period astrocytes exhibit amore elongated morphology under the same culture conditions and appear to be randomly dispersed among the endothelial cells. The scar astrocytes exhibit a wide range of morphologies and although they tend to cluster, do not exhibit the ordered association seen with the critical period astrocytes. We propose that the plasticity of the neonatal astrocytes and the rapid and ordered cellular response seen in vitro reflect the ability of the immature CNS in vivo to respond to injury without the formation of a glial-fibroblastic scar.

11. INDUCED REGENERATION OF CUT DORSAL ROOT FIBERS INTO ADULT RAT SPINAL CORD

Glial scar formation and inhibition by white matter are thought to impede sensory axons from regenerating across the dorsal root entry zone (DREZ) into the adult rat spinal cord. In order to assess the relative roles of these barriers, we unilaterally transected lumbar dorsal roots (L4-L6) and implanted the distal portion of L4 medially into the white matter of the dorsal columns or laterally just superficial to the gray matter of the dorsal horn. After three weeks, anterograde labelling with HRP demonstrated that many axons entered the spinal cord from laterally-implanted roots. A significant population of these axons entered the gray matter and formed terminal fields with synaptic boutons. Other axons extended into the white matter of the dorsal columns for variable distances. The placement of a specially designed Millipore filter, coated with embryonic astrocytes, just medial to the implanted root increased regeneration into the gray matter. Successful regeneration of axons was associated with a localized and limited inflammatory response near the sites of ingrowth. Axonal regeneration thus appears to be enhanced by the lateral placement of a transected sensory root, the use of an immature activated astrocyte-coated polymer, and the presence of a limited inflammatory response.

12. ANALYSIS OF NEONATAL AND ADULT RAT OLFACTORY BULB GLIAL CELL LINES

The rat olfactory bulb is reinnervated throughout life unlike other regions of the central nervous system, where glial differentiation effects loss of plasticity. In vitro, the differentiated phenotype of glial cells can be preserved by cell immortalization via oncogene transduction. We have used this approach to facilitate a study of the roles of glia in the innervation of the olfactory bulb.

Immortalized cell lines have been established from cultures of rat neonatal and adult olfactory bulbs and characterized concurrently with analogous primary cells. Two distinct phenotypes are evident within both neonatal and adult primary cultures: stellate, type I astrocyte-like, and fusiform (Anat. Record 210:385; Dev. Biol. 130:237) cells, each containing glial filaments. Both phenotypes are also present in uncloned immortalized cultures of neonatal and adult bulb.

Neurite outgrowth over monolayers of mature (adult) and neonatal cerebral cortical astrocyte cultures were compared to outgrowth over monolayers of adult olfactory fusiform and stellate GFAP+ clones, using a 24-hour neurite outgrowth assay with stage 31 chick retinal neurons. Mean neurite length was equivalent for adult fusiform olfactory cell lines (immortalized) and both the primary and immortalized immature cortical cells. In contrast, the mean length for the mature cortical astrocyte cells (both immortalized and primary cells) was reduced to the same extent as the reduction seen in immature cortical astrocyte cultures relative to primary immature cortical astrocyte cultures. These results suggest that: 1) the neurite promoting properties of glial cells are preserved through immortalization, and 2) the neurite promoting properties of adult olfactory glial cells and neonatal cerebral astrocytes are similar.

13. DEPOSIT OF MICROORGANISM

Murine embryonic astrocyte cell line mEASTR-2 (mouse embryonic astrocyte clone number two) was deposited with the American Type Culture Collection, Rockville, Md., on Feb. 1, 1989, and was assigned accession number CRL 10020.

The present invention is not to be limited in scope by the cell line deposited since the deposited embodiment is intended as a single illustration of one aspect of the invention and any cell lines which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various publications are cited herein, the disclosures of which are incorporated by reference in their entireties.

What is claimed is:

1. A method for promoting central nervous system axon regeneration comprising:
   (a) providing activated immature astrocytes; and
   (b) administering an effective amount of the activated immature astrocytes to damaged axons to promote axon regeneration.

2. The method according to claim 1, in which the activated immature astrocytes are stellate-shaped, GFAP-positive astrocytes.

3. The method according to claim 1, in which the activated immature astrocytes are embryonic through postnatal day 8 astrocytes.

4. The method according to claim 1 which further comprises before administering the activated immature astrocytes, substantially purifying the activated immature astrocytes.

5. The method according to claim 1, in which the activated immature astrocytes are immortalized astrocytes.

6. The method according to claim 1, in which the damaged axons are forebrain axons.

7. The method according to claim 1, in which the damaged axons are commissural axons.

8. The method according to claim 1, in which the damaged axons are spinal cord axons.

9. The method according to claim 8, in which the spinal axons are sensory axons.

10. The method according to claim 1, in which the damaged axons are in the dorsal root entry zone of the spinal cord.

11. The method according to claim 1, 3, 4, 5, 6 or 8 in which the astrocytes are brain astrocytes.

12. The method according to claim 11 in which the astrocytes are cerebral astrocytes.

13. A method for reducing glial scar formation in damaged central nervous system tissue comprising:
   (a) providing activated immature astrocytes; and
   (b) administering an effective amount of the activated immature astrocytes to damaged tissue of the central nervous system to reduce glial scar formation.

14. The method according to claim 13, in which the activated immature astrocytes are stellate-shaped, GFAP-positive astrocytes.

15. The method according to claim 13, in which the activated immature astrocytes are embryonic through postnatal day 8 astrocytes.

16. The method according to claim 13 which further comprises before administering the activated immature astrocytes, substantially purifying the activated immature astrocytes.

17. The method according to claim 13, in which the activated immature astrocytes are immortalized astrocytes.

18. The method according to claim 13, in which the damaged tissue of the central nervous system is a forebrain axon.

19. The method according to claim 18, in which the forebrain axon is a commissural axon.

20. The method according to claim 13, in which the damaged tissue of the central nervous system is a spinal cord axon.

21. The method according to claim 20, in which the spinal cord axon is a sensory axon.

22. The method according to claim 13, in which the damaged tissue of the central nervous system is in the dorsal root entry zone of the spinal cord.

23. The method according to claim 13, 15, 16, 17, 18 or 20 in which the astrocytes are brain astrocytes.

24. The method according to claim 23 in which the astrocytes are cerebral astrocytes.

25. A method for promoting blood vessel regeneration in the central nervous system comprising:
   (a) providing critical period activated immature astrocytes; and
   (b) administering an effective amount of the activated immature astrocytes to damaged blood vessels in the central nervous system to promote blood vessel regeneration.

26. The method according to claim 25, in which the activated immature astrocytes are stellate-shaped, GFAP-positive astrocytes.

27. The method according to claim 25, in which the activated immature astrocytes are embryonic through postnatal day 8 astrocytes.

28. The method according to claim 25, in which the activated immature astrocytes are immortalized astrocytes.

29. The method according to claim 25 which further comprises before administering the activated immature astrocytes, substantially purifying the activated immature astrocytes.

30. The method according to claim 25, in which the damaged blood vessels are in the forebrain.

31. The method according to claim 25, in which the damaged blood vessels are in the spinal cord.

32. The method according to claim 25, in which the damaged blood vessels are in the dorsal root entry zone of the spinal cord.

33. The method according to claim 25, 27, 28, 29, 30 and 31 in which the astrocytes are brain astrocytes.

34. The method according to claim 33, in which the astrocytes are cerebral astrocytes.

35. A method for treating a patient with nerve damage comprising administering an effective amount of activated immature astrocytes to the patient.

36. The method according to claim 35, in which the activated immature astrocytes are stellate-shaped, GFAP-positive astrocytes.

37. The method according to claim 35, in which the activated immature astrocytes are embryonic through postnatal day 8 astrocytes.

38. The method according to claim 35, in which the activated immature astrocytes are immortalized astrocytes.

39. The method according to claim 35, which further comprises before administering the activated immature astrocytes, substantially purifying the activated immature astrocytes.

40. The method according to claim 35, 36, 37, 38 or 39 in which the activated immature astrocytes are administered by seeding the astrocytes onto an implant, and inserting the seeded implant into the patient.

41. The method according to claim 35, 36, 37, 38 or 39 in which the activated immature astrocytes are administered in a media which partly impedes their mobility.

42. The method according to claim 35, 37, 38 or 39 in which the astrocytes are brain astrocytes.

43. The method according to claim 40, in which the astrocytes are brain astrocytes.

44. The method according to claim 42 in which the astrocytes are cerebral astrocytes.

45. The method according to claim 43 in which the astrocytes are cerebral astrocytes.

46. A method for treating a patient with nerve damage comprising administering an effective amount of olfactory bulb glial cells to the patient.

47. A pharmaceutical composition comprising isolated activated immature astrocytes; and a pharmaceutically acceptable sterile carrier for human administration.

48. The pharmaceutical composition of claim 47 in which the activated immature astrocytes are stellate-shaped, GFAP-positive astrocytes.

49. The pharmaceutical composition of claim 47 in which the activated immature astrocytes are embryonic through postnatal day 8 astrocytes.

50. The pharmaceutical composition of claim 47 in which the activated immature astrocytes are immortalized astrocytes.

51. The pharmaceutical composition of claim 47, 48, 49, or 50 in which the activated immature astrocytes are substantially purified.

52. The pharmaceutical composition of claim 47, 49, or 50 in which the astrocytes are brain astrocytes.

53. The pharmaceutical composition of claim 51 in which the astrocytes are brain astrocytes.

54. The pharmaceutical composition of claim 52 in which the astrocytes are cerebral astrocytes.

55. The pharmaceutical composition of claim 53 in which the astrocytes are cerebral astrocytes.

56. A pharmaceutical composition comprising isolated olfactory bulb glial cells; and a pharmaceutically acceptable sterile carrier for human administration.

57. The pharmaceutical composition of claim 56 in which the olfactory bulb glial cells are immortalized olfactory bulb glial cells.

* * * * *